United States Patent
Kitaura et al.

(10) Patent No.: US 10,393,649 B2
(45) Date of Patent: Aug. 27, 2019

(54) THZ BOLOMETER DETECTOR

(71) Applicant: HAMAMATSU PHOTONICS K.K., Hamamatsu-shi, Shizuoka (JP)

(72) Inventors: Ryusuke Kitaura, Hamamatsu (JP); Masatoshi Ishihara, Hamamatsu (JP); Masahiro Yamazaki, Hamamatsu (JP); Hironori Takahashi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/542,530

(22) PCT Filed: Jan. 13, 2016

(86) PCT No.: PCT/JP2016/050799
§ 371 (c)(1),
(2) Date: Jul. 10, 2017

(87) PCT Pub. No.: WO2016/114291
PCT Pub. Date: Jul. 21, 2016

(65) Prior Publication Data
US 2018/0266945 A1   Sep. 20, 2018

(30) Foreign Application Priority Data
Jan. 14, 2015   (JP) .................................. 2015-005256

(51) Int. Cl.
*G01N 21/35*   (2014.01)
*G01N 21/3581*   (2014.01)
(Continued)

(52) U.S. Cl.
CPC ............ *G01N 21/3581* (2013.01); *G01J 1/02* (2013.01); *G01J 1/0252* (2013.01); *G01J 3/42* (2013.01);
(Continued)

(58) Field of Classification Search
CPC ..... G01N 21/3581; G01J 1/0252; G01J 5/045
See application file for complete search history.

(56) References Cited

U.S. PATENT DOCUMENTS

| 6,292,140 B1 | 9/2001 | Osterman |
| 2006/0231761 A1 | 10/2006 | Peytavit et al. |

(Continued)

FOREIGN PATENT DOCUMENTS

| JP | 2000-337959 A | 12/2000 |
| JP | 2006-304290 A | 11/2006 |

(Continued)

OTHER PUBLICATIONS

International Preliminary Report on Patentability dated Jul. 27, 2017 for PCT/JP2016/050799.

(Continued)

*Primary Examiner* — Hugh Maupin
(74) *Attorney, Agent, or Firm* — Drinker Biddle & Reath LLP

(57) ABSTRACT

A THz bolometer detector includes a directional antenna 1 that receives a THz wave having a wavelength λ and radiates the received THz wave, a reception antenna 2 that is provided so as to face the directional antenna 1, and a bolometer 4 that detects heat generation due to a current flowing in the reception antenna 2. The directional antenna 1 overlaps the reception antenna 2 in plan view, and a longitudinal length of the directional antenna 1 is set to be less than a longitudinal length of the reception antenna 2.

7 Claims, 30 Drawing Sheets

(51) Int. Cl.
G01J 1/02 (2006.01)
G01R 29/08 (2006.01)
H01Q 19/30 (2006.01)
G01J 3/42 (2006.01)
G01J 5/08 (2006.01)
G01J 5/20 (2006.01)
G01J 5/24 (2006.01)
G01J 5/04 (2006.01)
H01Q 1/24 (2006.01)
H01Q 1/38 (2006.01)

(52) U.S. Cl.
CPC ............. *G01J 5/045* (2013.01); *G01J 5/08* (2013.01); *G01J 5/0837* (2013.01); *G01J 5/20* (2013.01); *G01J 5/24* (2013.01); *G01R 29/08* (2013.01); *H01Q 1/24* (2013.01); *H01Q 1/38* (2013.01); *H01Q 19/30* (2013.01)

(56) References Cited

U.S. PATENT DOCUMENTS

2011/0248724 A1 10/2011 Sekiguchi
2012/0091342 A1* 4/2012 Berger .................. G01J 5/0837
250/338.4
2013/0082181 A1* 4/2013 Corcos .................... G01J 5/34
250/349
2014/0117241 A1 5/2014 Corcos et al.

FOREIGN PATENT DOCUMENTS

| JP | 2010-166227 A | 7/2010 |
| JP | 2010-261935 A | 11/2010 |
| JP | 2011-222833 A | 11/2011 |
| JP | 5109169 B2 | 12/2012 |
| WO | WO 2011/048170 A1 | 4/2011 |
| WO | WO-2011/142191 A1 | 11/2011 |

OTHER PUBLICATIONS

Kuntae Kim et al., "Fabrication and characterization of a three-dimensional feed-horn infrared antenna for an infrared detector," Applied Optics, Oct. 20, 2004, pp. 5594-5599, vol. 43, No. 30.

Katsunari Irie et al., "Proposal and Design of Thin Film Laminated Photoconductive Antenna with Yagi-Uda Array Fabricated by Pattern Plating Transfer Process," The 60th JSAP Spring Meeting Koen Yokoshu, 2013, p. 28-D1-4, including partial English translation.

* cited by examiner

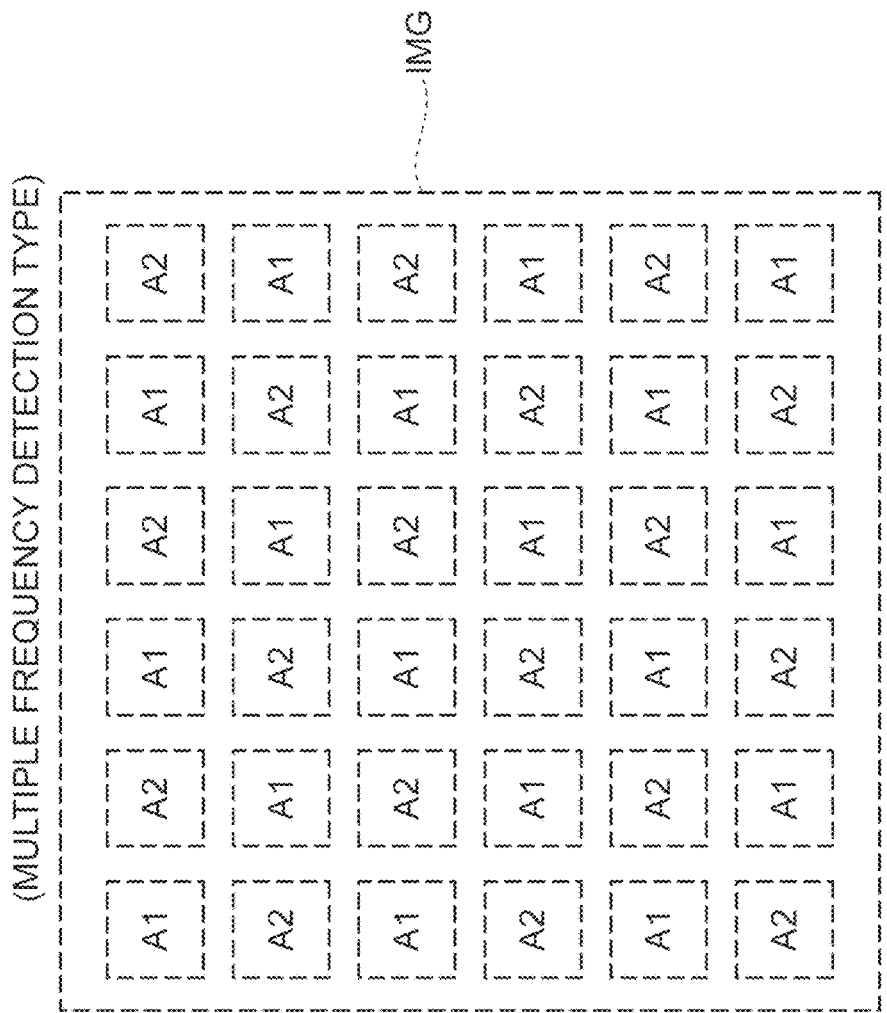
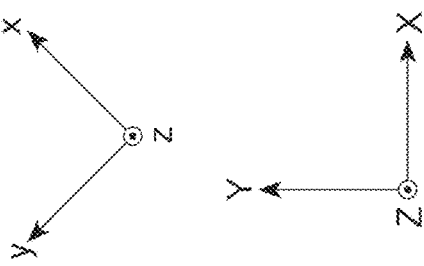
Fig.21

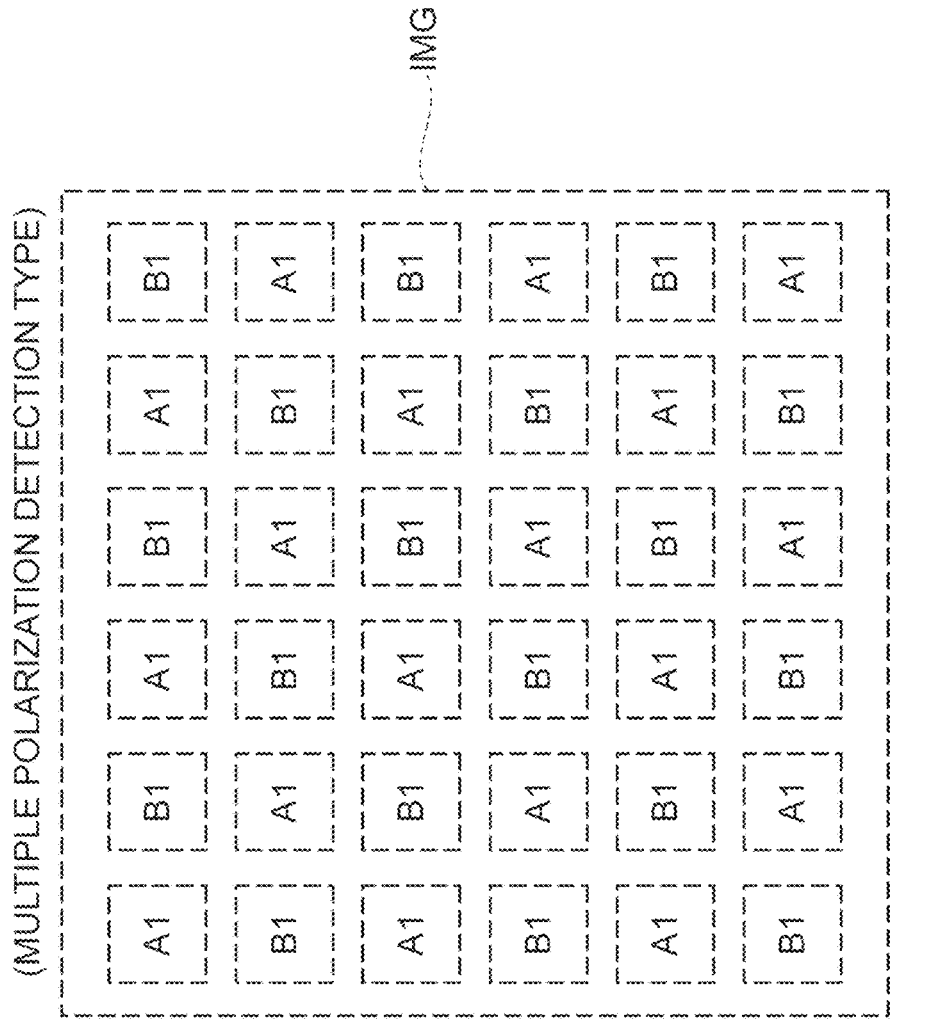
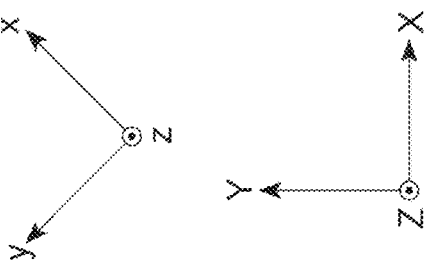
Fig.22

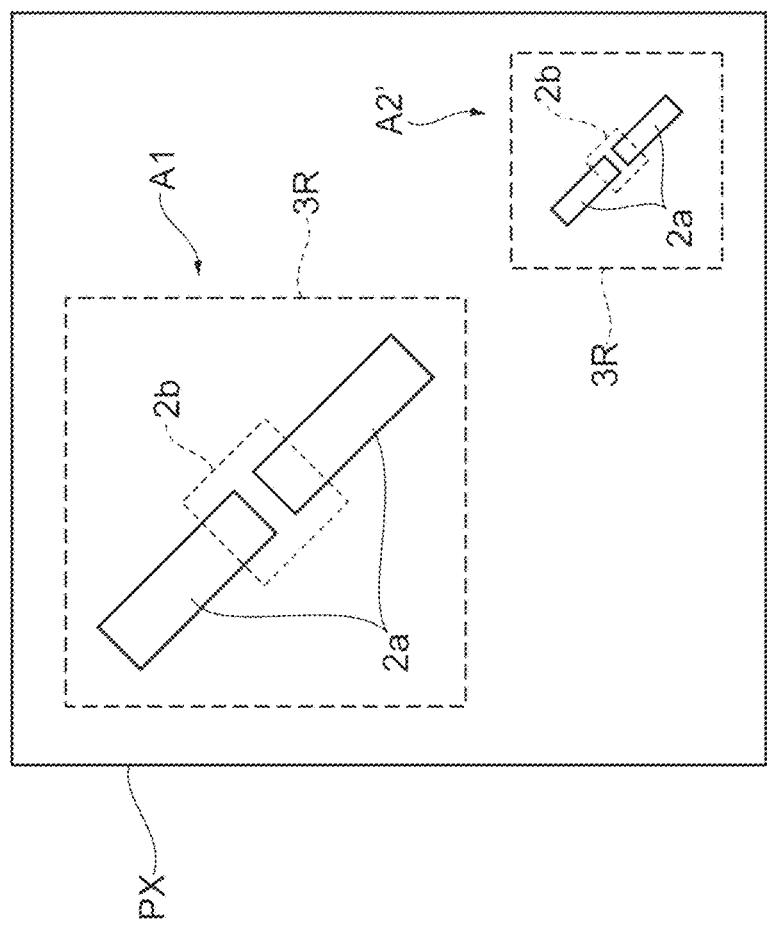
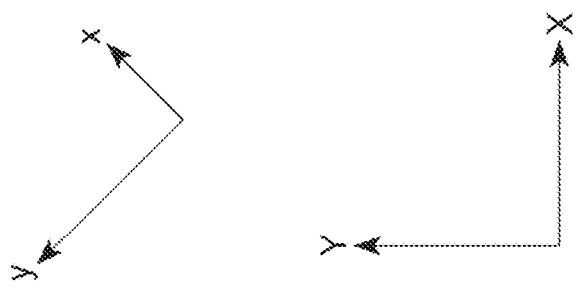
Fig.28

THZ BOLOMETER DETECTOR

TECHNICAL FIELD

The present invention relates to a THz bolometer detector.

BACKGROUND ART

A bolometer is a heat (infrared) detecting element that uses properties of a resistor (or a conductor) of which a resistance value is changed depending on a temperature change, and is called a thermistor in a case where a temperature change rate of the resistor is high.

A THz bolometer detector is a device that detects an electromagnetic wave (THz wave) having a terahertz frequency band (wavelength λ is equal to or greater than 30 μm and is equal to or less than 1 m), and is expected to be applied to a material analysis technique (see, for example, Patent Literature 1 and Patent Literature 2). In the detector described in the literature, the THz wave is absorbed by an absorbing film or the THz wave is received by an antenna. The generated heat is input to the bolometer, and thus, the THz wave is indirectly detected.

CITATION LIST

Patent Literature

[Patent Literature 1] Japanese Patent No. 5109169
[Patent Literature 2] Japanese Unexamined Patent Publication No. 2010-261935

SUMMARY OF INVENTION

Technical Problem

However, a THz bolometer detector capable of detecting a weaker electromagnetic wave than that in the THz bolometer detector of the related art is expected.

The invention has been made in view of such problems, and it is an object of the invention to provide a THz bolometer detector capable of detecting a weak electromagnetic wave.

Solution to Problem

In order to solve the above-described problems, there is provided a THz bolometer detector including: a directional antenna that receives a THz wave, and radiates the received THz wave; a reception antenna that is provided so as to face the directional antenna; and a bolometer that detects heat generation due to a current flowing in the reception antenna. The directional antenna overlaps the reception antenna in plan view, and a longitudinal length of the directional antenna is less than a longitudinal length of the reception antenna.

Since the directional antenna is shorter than the reception antenna, the THz wave incident on the directional antenna is re-radiated after the phase thereof is changed, and is received by the reception antenna. Since the directional antenna overlaps the reception antenna in plan view and the reception antenna is able to be provided in a position in which a large electric field amplitude is received through the phase adjustment using the directional antenna, a large current flows in response to the reception, and heat is generated by the resistor (or a conductor). Since the amount of generated heat is detected by the bolometer, this device functions as the THz bolometer detector. In a case where the longitudinal direction of the directional antenna and the longitudinal direction of the reception antenna match each other, the reception antenna can receive a larger electric field amplitude.

A wavelength of the THz wave is λ, and a distance between the directional antenna and the reception antenna is equal to or less than λ/4 (equivalent to π/2 as a phase). In this case, since the THz wave incident on the reception antenna and the THz wave re-radiated from the directional antenna have the same phase on an incident side of the reception antenna, these THz waves reinforce each other. Since these THz waves have reversed phases to each other on an opposite side, these antennas have strong directivity on the incident side.

The THz bolometer detector further includes: a reflection antenna that is provided in a position where the reception antenna is interposed between the reflection antenna and the directional antenna. In a case where the THz wave is incident on the reflection antenna, since the re-radiated THz wave is able to be incident on the reception antenna, a position of the reflection antenna is appropriately adjusted, and thus, it is possible to increase the electric field amplitude received by the reception antenna.

The THz bolometer detector further includes: a lid member that includes a recess portion; and a support substrate that is covered with the lid member, and defines an enclosed space in cooperation with the lid member. The directional antenna is fixed to a bottom surface of the recess portion, and the directional antenna, the reception antenna, and the bolometer are provided within the enclosed space.

A detector which compactly accommodates an antenna group in the enclosed space, has a high tolerance to an environment change, and has a small size can be constituted.

The lid member includes a silicon substrate having the recess portion, a depth d1 of the recess portion of the silicon substrate is equal to or greater than 10 μm and is equal to or less than 400 μm, a thickness d2 of a peripheral portion of the silicon substrate is equal to or greater than 200 μm and is equal to or less than 2 mm, and a pressure less than an atmospheric pressure is set within the enclosed space. The pressure lower than the atmospheric pressure is preferably vacuum (0.1 Pa or less), and thus, it is possible to perform detection having high environment tolerance with high sensitivity. Since the recess portion is formed in the silicon substrate, the silicon substrate is likely to be deformed by a pressure difference. Here, the silicon substrate can be prevented from being deformed by setting the depth of the recess portion to be equal to or greater than a lower limit of the numeric range, and it is possible to suppress high attenuation of the THz wave by setting the thickness to be equal to or less than an upper limit.

The THz bolometer detector further includes: an anti-reflection film that is formed on a surface opposite to the recess portion of the silicon substrate; and an insulation film that is formed on an internal surface of the recess portion of the silicon substrate. A material of the anti-reflection film is $SiO_2$ or poly(para-xylylene) (parylene (registered trademark)), a material of the insulation film is $SiO_2$ or poly(para-xylylene), and a resistivity of the silicon substrate is set to be equal to or greater than 1 kΩcm.

In this case, since the reflection of the THz wave is suppressed by the anti-reflection film and the amount of impurities is small within the silicon substrate, the attenuation of the THz wave is low, and thus, the THz wave can be sufficiently incident on the directional antenna.

Advantageous Effects of Invention

According to the THz bolometer detector of the present invention, since a large electric field amplitude is received, it is possible to detect a weak electromagnetic wave.

BRIEF DESCRIPTION OF DRAWINGS

FIG. 21 is a diagram showing an arrangement example of the unit sensors (pixels) in the capturing area IMG.

FIG. 22 is a diagram showing an arrangement example of the unit sensors (pixels) in the capturing area IMG.

FIG. 28 is a plan view of a unit pixel including the plurality of unit sensors.

DESCRIPTION OF EMBODIMENTS

Hereinafter, a THz bolometer detector according to an embodiment will be described. The same elements will be assigned to the same reference signs, and thus, the redundant description thereof will be omitted.

Figure 1:
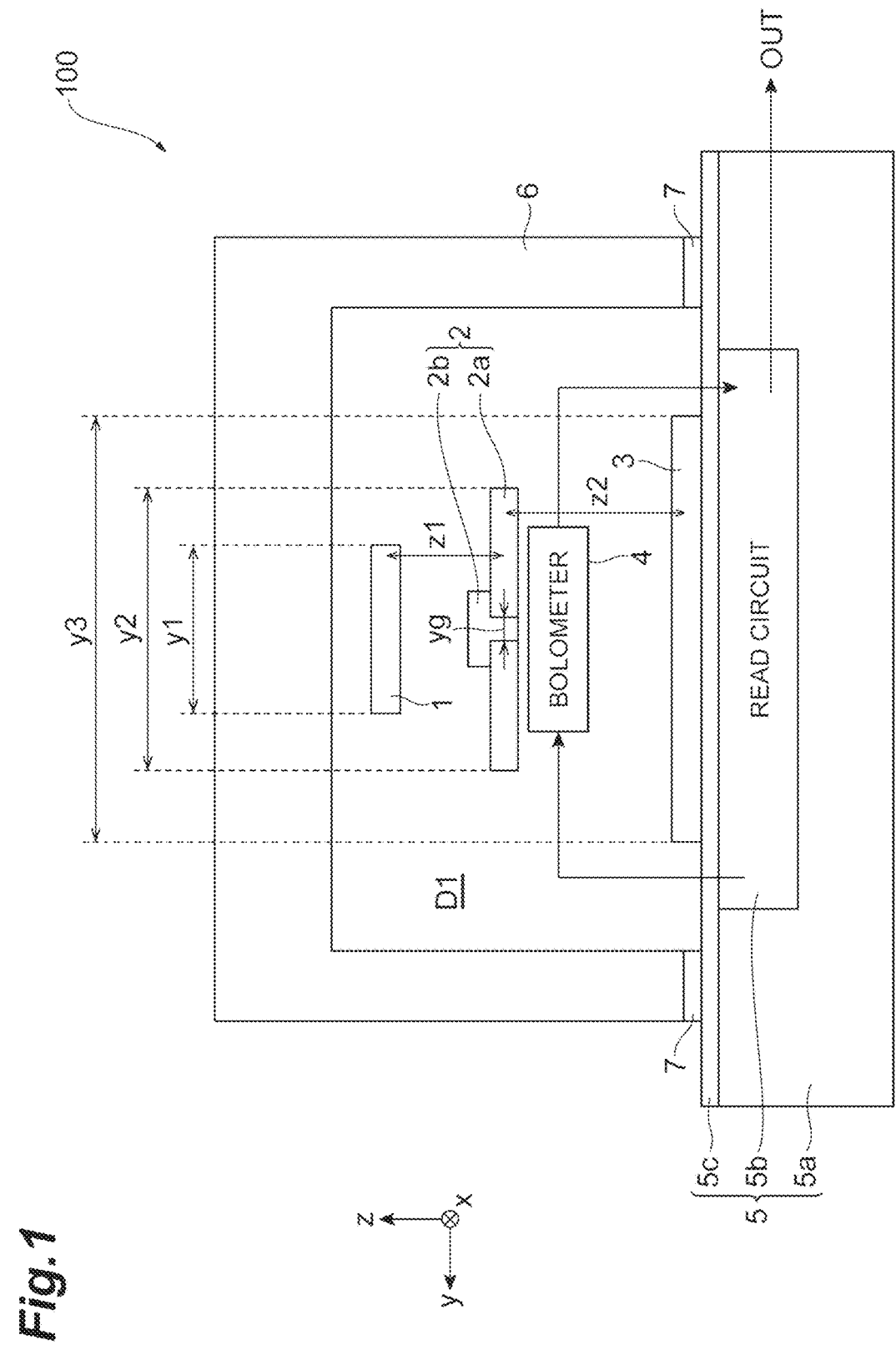
FIG. 1 is a diagram showing a structure of a THz bolometer detector according to a first embodiment.

FIG. 1 is a diagram showing a structure of a THz bolometer detector 100 according to a first embodiment.

Figure 5:
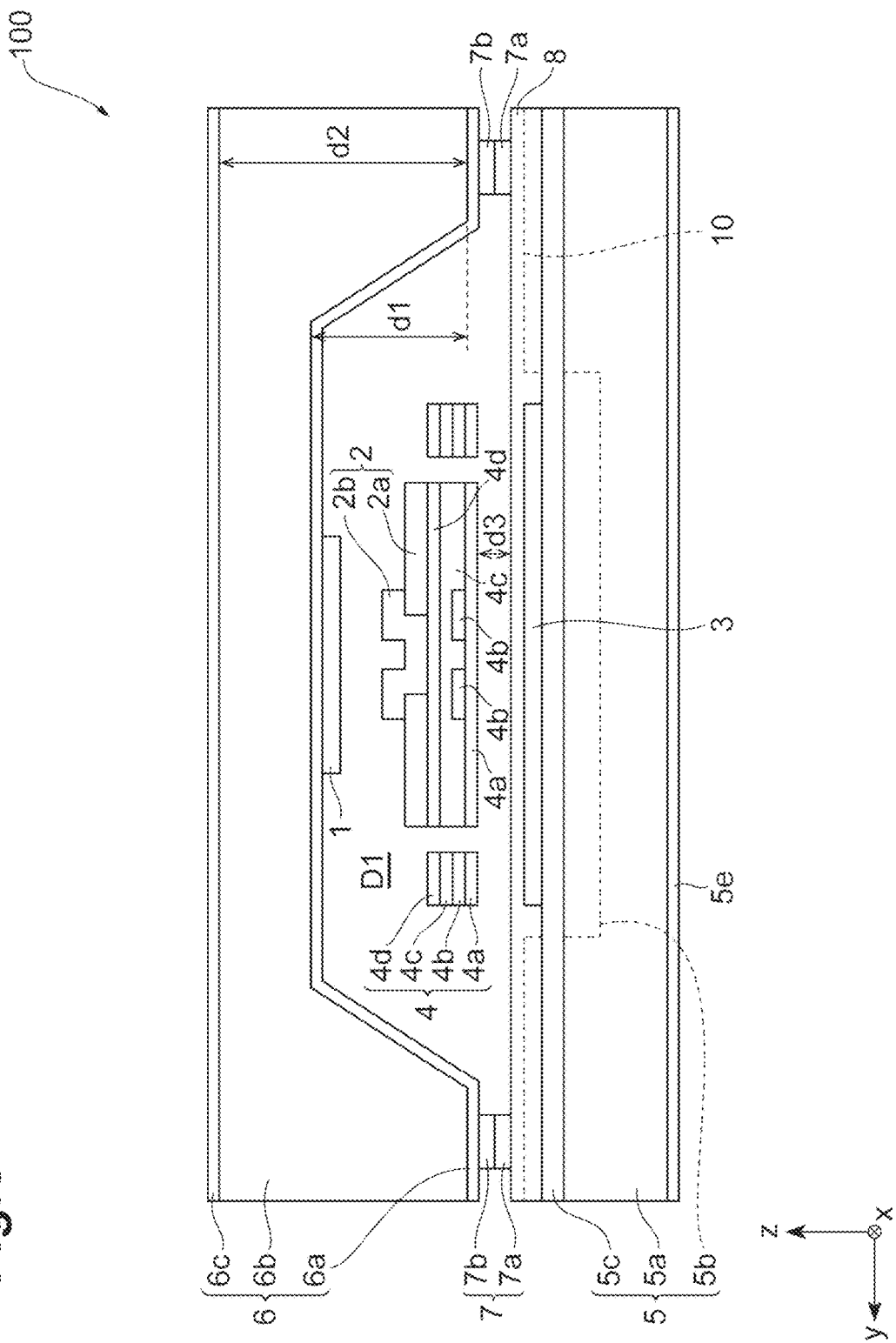
FIG. 5 is a diagram showing a sectional structure of the THz bolometer detector.

The THz bolometer detector 100 includes a lid member 6 including a recess portion D1, and a support substrate 5 that is covered with the lid member 6 and defines an enclosed space including the recess portion D1 in cooperation with the lid member 6. A directional antenna 1, a reception antenna 2, a reflection antenna 3, and a bolometer 4 are provided within the enclosed space. The device becomes compact in a case where the directional antenna 1 is fixed to a bottom surface of the recess portion D1 as shown in FIG. 5. A detector which compactly accommodates an antenna group in the enclosed space, has high tolerance to an environment change, and has a small size is constituted. A sealing member 7 is provided between the lid member 6 and the support substrate 5. The support substrate 5 is an integrated circuit board, and a read circuit 5b is provided in the support substrate. The support substrate 5 includes a semiconductor substrate 5a, the read circuit 5b formed in the semiconductor substrate 5a, and an insulation film 5c that coats a front surface of the semiconductor substrate 5a.

A material of the semiconductor substrate 5a may be silicon, a material of the insulation film 5c may be $SiO_2$ or SiNx, and a material of the sealing member 7 may be at least any one selected from a metal group consisting of indium, copper, tin, and gold. Other materials may be used. In the present example, it is assumed that Au/AuSn is used as the sealing member 7.

The directional antenna 1 receives the THz wave and radiates the received THz wave, and the reception antenna 2 is provided so as to face the directional antenna 1. The reflection antenna 3 reflects the THz wave transmitted through the reception antenna 2, and the bolometer 4 detects heat generation due to a current flowing in the reception antenna 2.

Here, it is assumed that a longitudinal direction of the directional antenna 1 is a y-axis direction, a width direction of the directional antenna 1 is an x-axis direction, and a thickness direction of the directional antenna 1 is a z-axis direction by setting an xyz three-dimensional coordinate system. In a case where the directional antenna 1 present within an xy plane is observed in the z-axis direction, that is, in plan view, the directional antenna 1 overlaps the reception antenna 2, and a longitudinal length (y1) of the directional antenna 1 is less than a longitudinal length (y2) of the reception antenna 2.

Since the directional antenna 1 is shorter than the reception antenna 2, the phase of the THz wave incident on the directional antenna 1 from an upward position of the drawing through the lid member 6 are changed. The THz wave is re-radiated by the directional antenna 1, and is received by the reception antenna 2.

The reception antenna 2 includes a dipole antenna 2a including a pair of linear antennas, and a resistor 2b provided in a gap between the linear antennas constituting the dipole antenna 2a. For example, this gap yg may be set to be equal to or less than 10 µm. The resistor 2*b* electrically connects the pair of linear antennas, and generates heat due to a current flowing in these antennas.

Since the directional antenna 1 overlaps the reception antenna 2 in plan view and the reception antenna 2 is able to be provided in a position in which a large electric field amplitude is received through phase adjustment using the directional antenna 1, a large current flows in response to the reception, and heat is generated by the resistor 2*b* (or the conductor). Since the amount of generated heat is detected by the bolometer 4 provided so as to be close to the reception antenna 2, this device functions as the THz bolometer detector.

Figure 9:
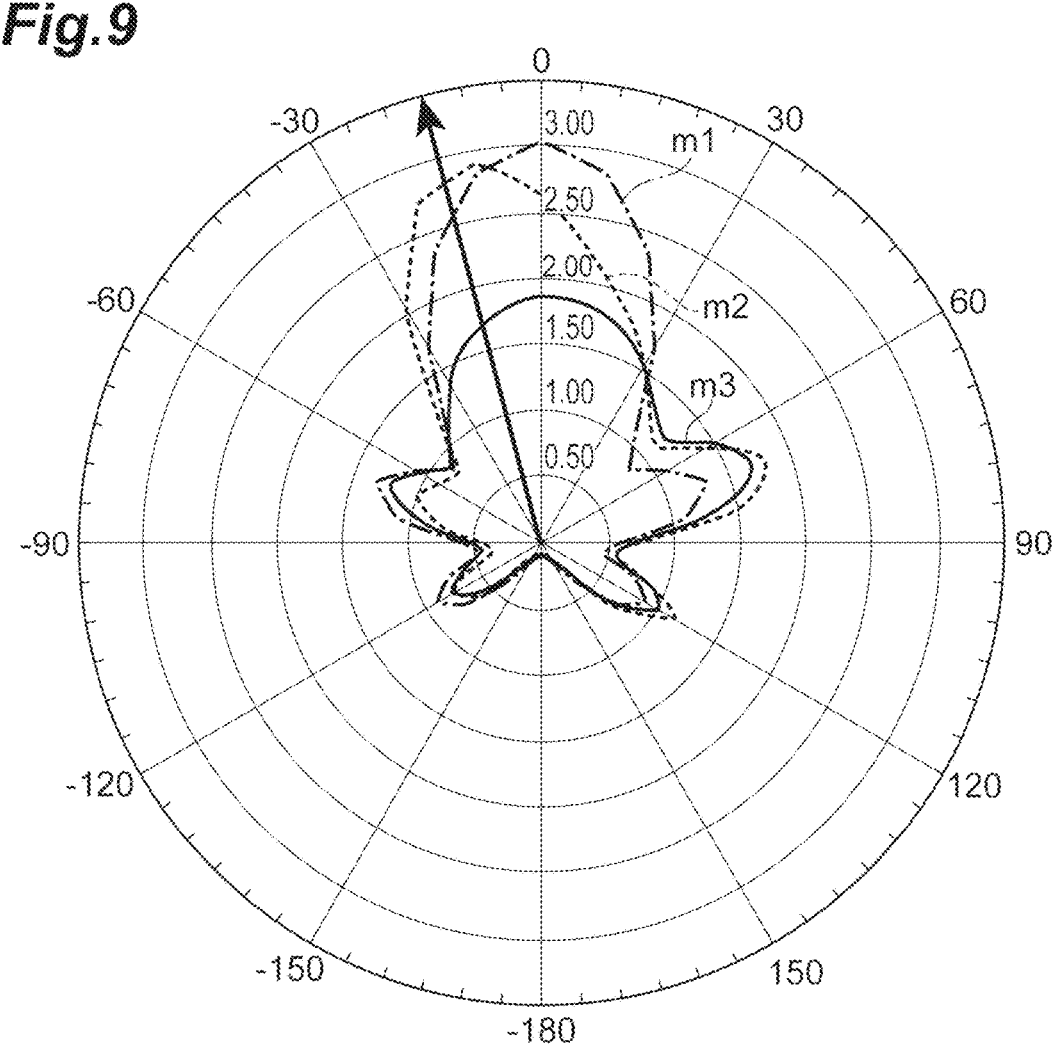
FIG. 9 is a diagram showing a radiation pattern of an antenna of which a position in an x-axis direction is changed.
Figure 10:
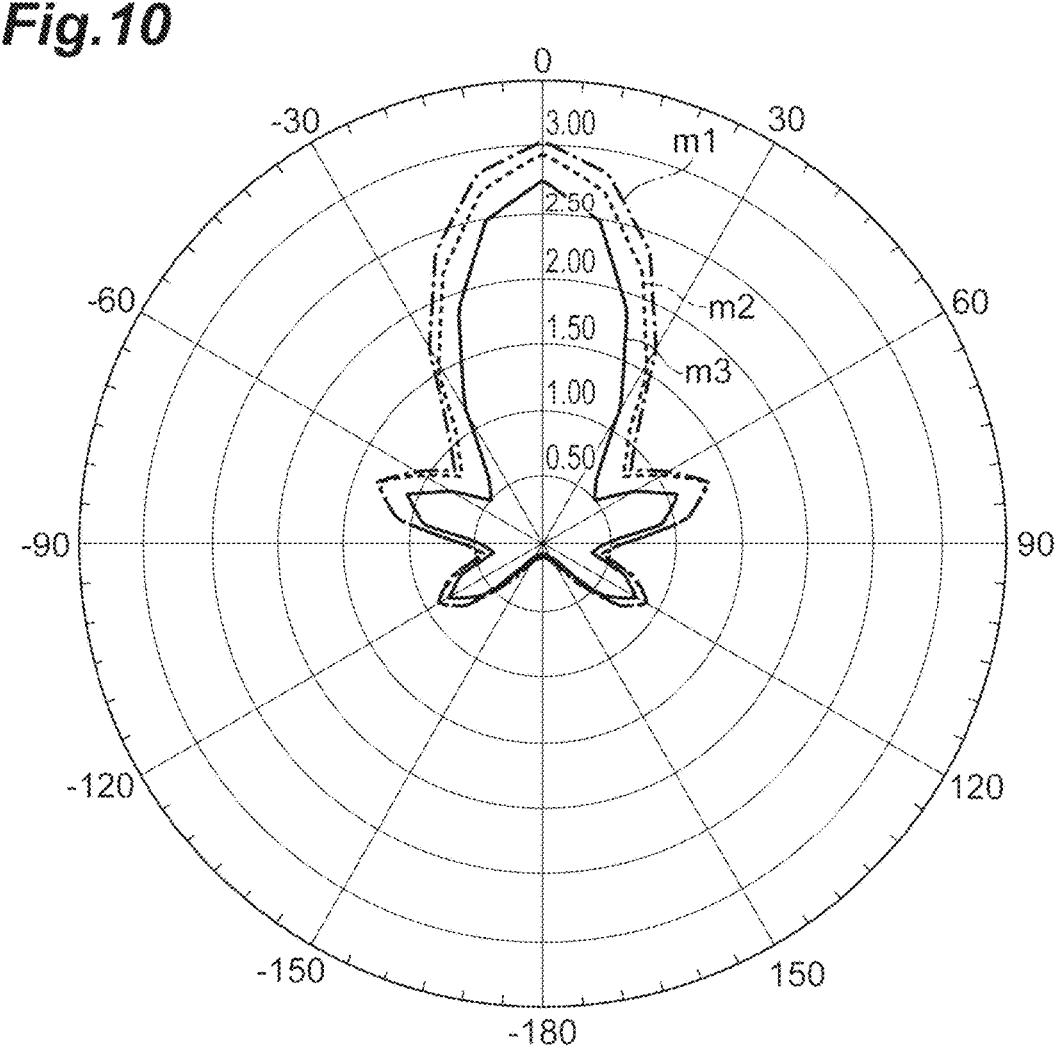
FIG. 10 is a diagram showing a radiation pattern of the antenna of which the position in the y-axis direction is changed.

The longitudinal direction (y-axis direction) of the directional antenna 1 and the longitudinal direction (y-axis direction) of the reception antenna 2 match each other, and the reception antenna may receive a large electric field amplitude as shown in FIGS. 9 and 10.

That is, FIG. 9 is a diagram showing a radiation pattern of the antenna of which the position in the x-axis direction is changed, and FIG. 10 is a diagram showing a radiation pattern of the antenna of which the position in the y-axis direction is changed. A scale of a circumferential direction represents an angle, and a center position of a circle is a center position of gravity of the reception antenna 2. A direction from the center position to −90° is a +x-axis direction, and a direction from the center position to 0° is a +z-axis direction. A scale in a radial direction is an absolute gain of the antenna, and a unit is dB. An arrow in FIG. 9 represents a change in a directivity maximum direction when the directional antenna 1 is shifted with respect to the reception antenna 2 by 7 µm from a reference state in the x-axis direction.

In the reference state, a center position of gravity of the directional antenna 1 and the center position of gravity of the reception antenna 2 match each other (x=0 µm), and the longitudinal directions and the width directions thereof also match each other (y=0 µm).

If the directional antenna 1 is shifted from the reference state (data m1 (x=0 µm) of FIG. 9) in the x-axis direction (m2: x=7 µm, m3: x=15 µm), reception efficiency is decreased (FIG. 9). That is, in a case where the directional antenna 1 is shifted with respect to the reception antenna 2 in the x-axis direction, a distance z1 between the center positions of gravity of these antennas is changed to z1' (z1'=(z1$^2$+x$^2$)$^{1/2}$). Accordingly, if the phases of the THz wave incident on the reception antenna 2 and the THz wave re-radiated from the directional antenna 1 are shifted and a resonance effect is diminished, the reception efficiency is decreased by a loss due to a change in mutual impedance.

If the directional antenna 1 is shifted from the reference state (data m1 (x=0 µm) of FIG. 10) in the y-axis direction (m2: y=7 µm, m3: y=15 µm), the reception efficiency is decreased (FIG. 10). That is, in a case where the directional antenna 1 is shifted with respect to the reception antenna 2 in the y-axis direction, the reception efficiency is decreased by a loss due to a change in mutual impedance caused by a change of a positional relationship.

As stated above, in a case where positions of the directional antenna 1 and the reception antenna 2 are shifted from the reference state, since a reception loss occurs, it is preferable that the positional relationship between these antennas is the reference state. The loss due to the shift in the x-axis direction is greater than the loss due to the shift in the y-axis direction.

It is assumed that a wavelength of the THz wave is 2. The distance z1 between the directional antenna 1 and the reception antenna 2 is equal to or less than λ/4 (equivalent to π/2 as a phase). The distance z1 is a distance between the center positions of gravity in the reference state, and is a z-axis direction distance between the center positions of gravity in a case where the positions of the antennas are shifted in the x-axis or the y-axis direction. In this case, since the THz wave incident on the reception antenna 2 and the THz wave re-radiated from the directional antenna 1 have the same phase on an incident side of the reception antenna 2, these THz waves reinforce each other. Since these THz waves have reversed phases to each other on an opposite side, these antennas have strong directivity on the incident side.

The reflection antenna 3 is provided in a position where the reception antenna 2 is interposed between the reflection antenna and the directional antenna 1. In a case where the THz wave is incident on the reflection antenna 3, since the re-radiated THz wave is able to be incident on the reception antenna 2, a distance z2 between these antennas, that is, a position of the reflection antenna 3 is appropriately adjusted, and thus, it is possible to increase the electric field amplitude received by the reception antenna 2.

It is possible to constitute the antenna group by using the dipole antenna overlapping in plan view, and thus, directivity for the THz wave incident from above a sensor is increased due to a mutual effect. As a result, it is possible to increase the reception efficiency of the reception antenna 2. Here, the reception antenna 2 includes a power supply point (resistor), but the directional antenna 1 and the reflection antenna 3 are passive elements that do not include the power supply point.

If the wavelength of the incident THz wave is λ, the length y2 of the reception antenna 2 is equal to or less than λ/2. Power in the resistor 2*b* provided in the power supply point in the center of the antenna due to electromotive force generated depending on optical intensity of the THz wave incident on the reception antenna 2 is consumed, and thus, heat is generated.

The directional antenna 1 is the passive element formed above (on the THz wave incident side of) the reception antenna 2, and since the length y1 thereof is less than the length y2 of the reception antenna 2 (y1<y2), y1 is less than λ/2.

The distance between the reception antenna 2 and the directional antenna 1 is equal to or less than λ/4, and an induced current flows in the directional antenna 1 due to the THz wave incident from above, and the THz wave is re-radiated. In this case, since the re-radiated wave and the incident wave have the same phase above a membrane in which the reception antenna 2 is provided, these waves reinforce each other. Since these waves have reversed phases to each other under the membrane, these waves weaken each other. Thus, the directivity of the reception antenna 2 for the THz wave incident from above becomes strong, and thus, the reception efficiency of the reception antenna can be increased.

The reflection antenna 3 is the passive element formed under (opposite side to the THz wave incident side of) the reception antenna 2. A length y3 of the reflection antenna 3 is set to be longer than the length of the reception antenna (y2<y3). The distance z2 between the center positions of gravity of the reception antenna 2 and the reflection antenna 3 in the z-axis direction is equal to or less than λ/4. Similarly to the case of the directional antenna 1, an induced current flows in the reflection antenna 3 due to the THz wave incident from above, and the THz wave is re-radiated. Since the re-radiated wave and the incident wave have the same phase above the membrane, these waves reinforce each other. Since these waves have reversed phases to each other under the membrane, these waves weaken each other. Thus, the directivity of the reception antenna 2 for the THz wave incident from above becomes strong, and thus, the reception efficiency of the reception antenna can be further increased.

Figure 2:
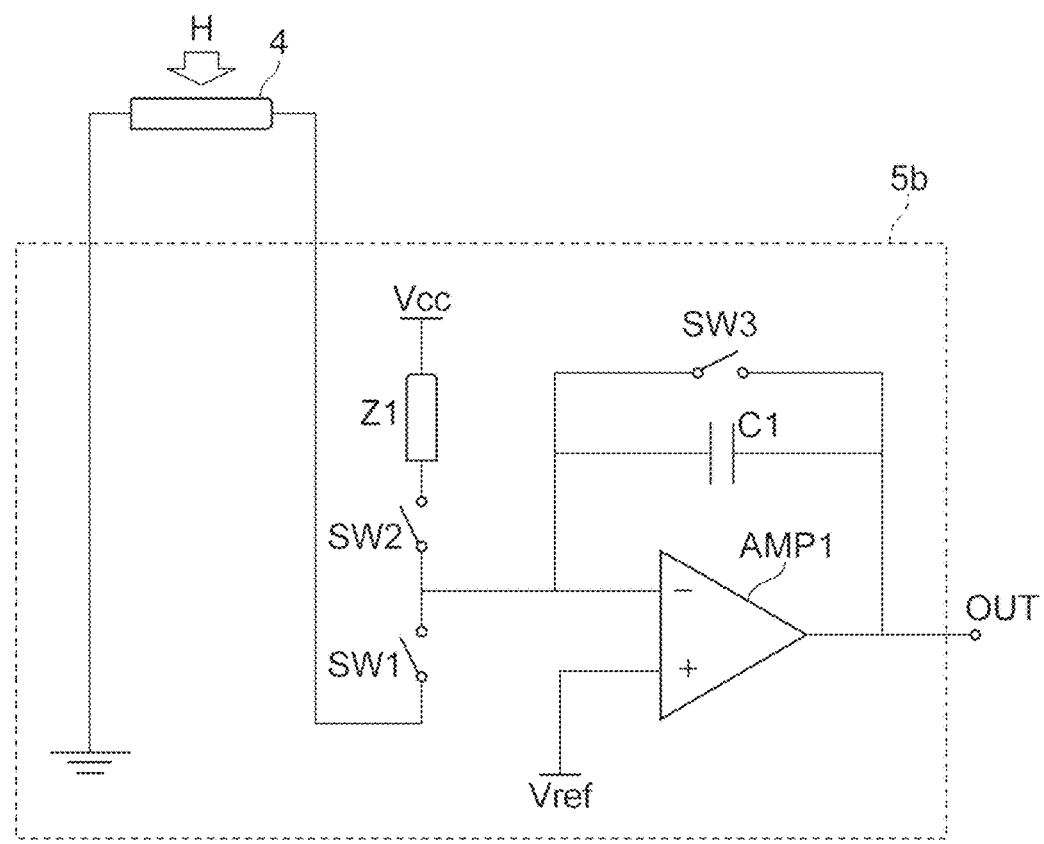
FIG. 2 is a circuit diagram of a read circuit.

FIG. 2 is a circuit diagram of the read circuit 5b. The connection in the circuit means electrical connection.

Heat H generated in the resistor of the reception antenna 2 is incident on the bolometer 4. A primary constituent element of the bolometer 4 is a resistor. An output of the bolometer 4 is input to an amplifier AMP1 through a switch SW1, and an output signal OUT is output from an output terminal of the amplifier AMP1. A capacitor C1 and a switch SW3 are connected in parallel between an inverting input terminal and the output terminal of the amplifier AMP1, and a reference potential Vref is connected to a non-inverting input terminal. The non-inverting input terminal is connected to a connection point between the switch SW1 and a switch SW2, and the connection point is connected to a power supply potential Vcc through the switch SW2 and a resistor Z1. If the switch SW3 is closed, the circuit enters a reset state, and the capacitor C1 is discharged. After the switch SW3 is opened, if the switches SW1 and SW2 are closed, a current flows to the bolometer 4 from the power supply potential Vcc. Thus, a value depending on a resistance value is input to the non-inverting input terminal of the amplifier AMP1, an electric charge is accumulated in the capacitor C1, and the output signal OUT is acquired from the output terminal.

Hereinafter, the relationship between the electric field amplitude and the position will be described in detail. Initially, a phenomenon occurring in the installation of the directional antenna 1 will be described.

Figure 3:
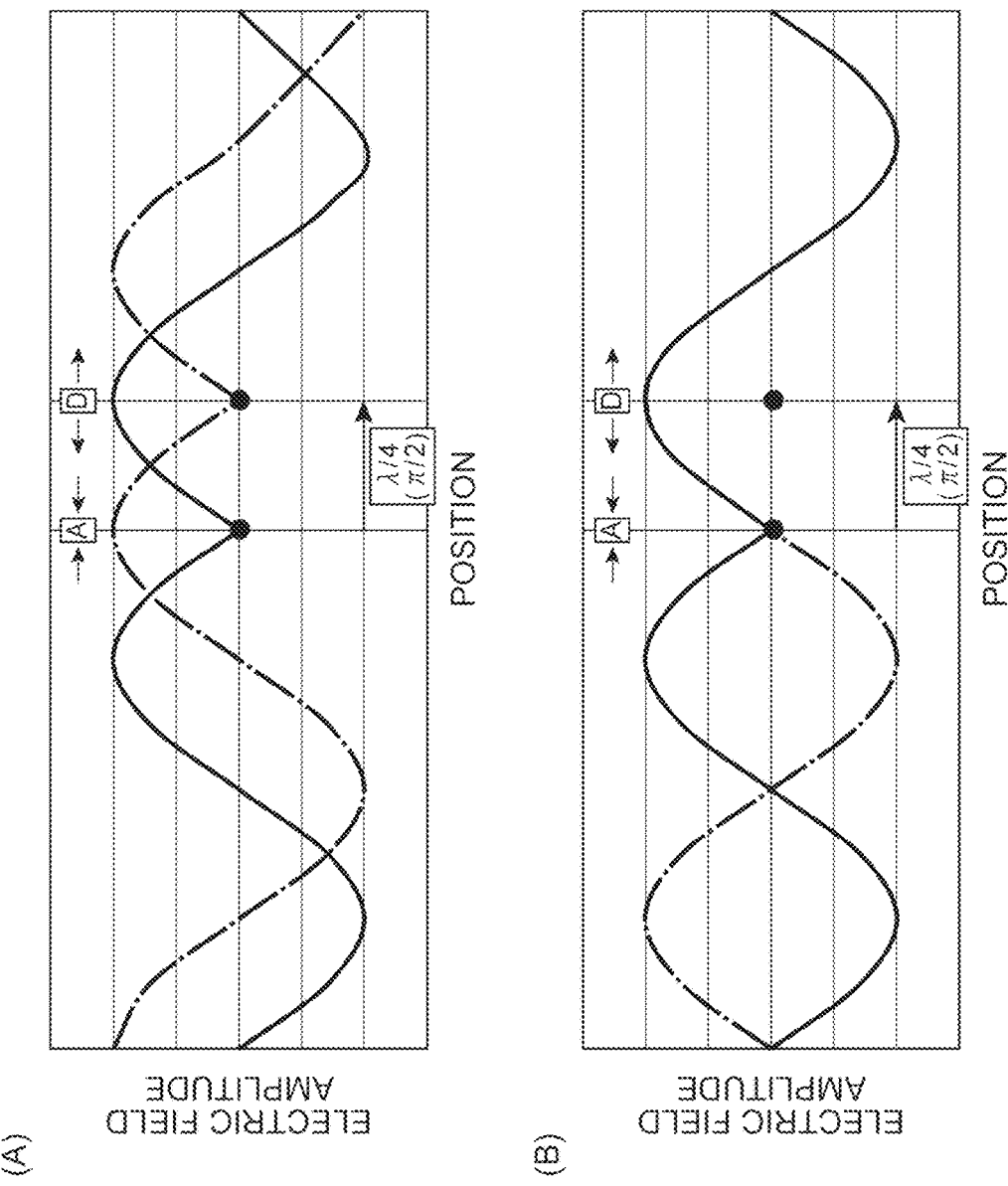
FIG. 3-(A) and FIG. 3-(B) are graphs showing the relationship between a position and an electric field amplitude.

FIG. 3 is a graph showing the relationship between a position and an electric field amplitude. It is assumed that the THz wave is incident from the right side of the drawing.

FIG. 3-(A) is a graph in a case where the lengths of the directional antenna 1 and the reception antenna 2 are equal to each other, and FIG. 3-(B) is a graph in a case where the directional antenna 1 is shorter than the reception antenna 2. A horizontal axis in the graph represents a position along the z-axis direction, and a vertical axis represents an electric field amplitude. The directional antenna 1 is provided in a position of D in the drawing, and the reception antenna 2 is provided in a position of A. A separation distance between these antennas is $\lambda/4$, and the above-described effect is acquired even though this separation distance is less than $\lambda/4$.

This drawing shows the relationship between the THz wave (solid line) incident on the reception antenna 2 and the THz wave (dashed-dotted line) re-radiated from the directional antenna 1 in a state in which the reception antenna 2 and the directional antenna 1 are horizontally provided. Here, it is assumed that the length y2 of the reception antenna 2 is $\lambda/2$, a reactance component of the reception antenna 2 is $0\Omega$, and the distance z1 between the reception antenna 2 and the directional antenna 1 is $\lambda/4$.

It is preferable that the antenna length or the distance between these antennas is slightly less than the dimension in consideration of matching of impedance changed due to an antenna surrounding medium, a resistance component of an antenna wiring, an antenna width, or a mutual operation when two antennas approach each other.

In the case of FIG. 3-(A), electromotive force is generated according to Maxwell and Ampere's law by a magnetic field of the THz wave incident on the directional antenna 1, and an induced current flows. In this case, since the length of the directional antenna 1 is equal to that of the reception antenna and the reactance component is 0, the electromotive force and the induced current have the same phase, and the THz wave re-radiated from the directional antenna by the induced current and the incident THz wave have the same phase. Thus, the THz wave incident on the reception antenna 2 and the THz wave re-radiated from the directional antenna 1 are shifted by a phase of $\pi/2$, as shown in FIG. 3-(A).

In the case of FIG. 3-(B), since the length of the directional antenna 1 is less than that of the reception antenna 2, the directional antenna has a capacitive reactance component, the phase of the induced current flowing due to the THz wave incident on the directional antenna 1 further proceeds than that of the electromotive force by $\pi/2$. The phase of the THz wave re-radiated from the directional antenna 1 by the induced current further proceeds than that of the incident THz wave by $\pi/2$. The distance z1 between the reception antenna 2 and the directional antenna 1 is set to be $\lambda/4$ (that is, equivalent to $\pi/2$ as the phase). Thus, since the THz wave incident on the reception antenna 2 and the THz wave re-radiated from the directional antenna 1 have the same phase on the incident side of the reception antenna 2, these waves reinforce each other. Since these waves have reversed phases to each other, these waves weaken each other. As a result, the incident side has strong directivity.

Hereinafter, a phenomenon occurring in the installation of the reflection antenna will be described.

Figure 4:
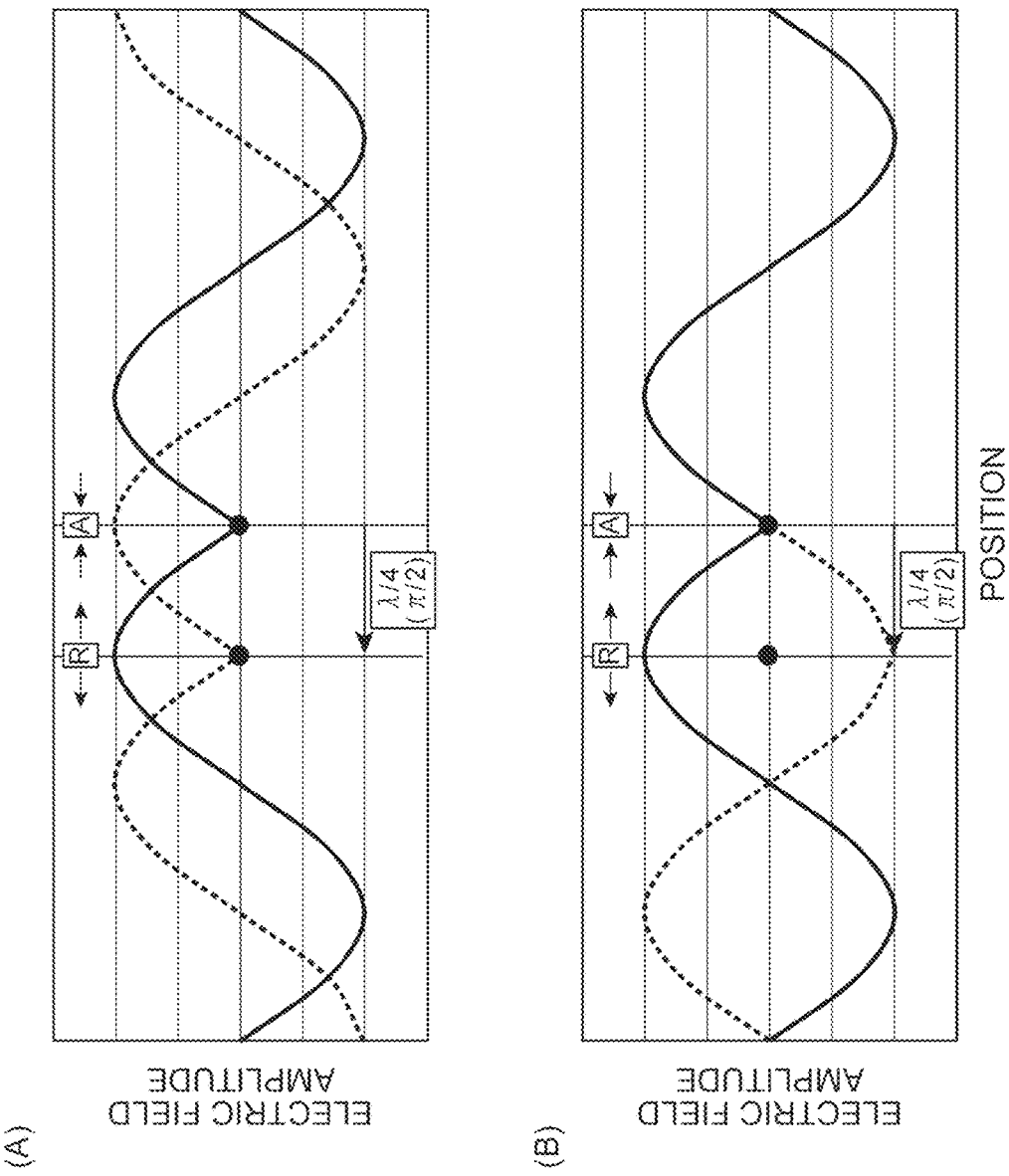
FIG. 4-(A) and FIG. 4-(B) are graphs showing the relationship between a position and an electric field amplitude.

FIG. 4 is a graph showing the relationship between a position and an electric field amplitude. It is assumed that the THz wave is incident from the right side of the drawing. The relationship between the THz wave incident on the reception antenna 2 and the THz wave re-radiated from the reflection antenna 3 is illustrated. A horizontal axis in the graph represents a position along the z-axis direction, and a vertical axis represents an electric field amplitude. The reflection antenna 3 is provided in a position of R in the drawing, and the reception antenna 2 is provided in a position of A. A separation distance between these antennas is $\lambda/4$, and the above-described effect is acquired even though this separation distance is less than $\lambda/4$.

The length of the reception antenna 2 is set to be $\lambda/2$, the reactance component of the reception antenna 2 is set to be $0\Omega$, and the distance z2 between the reception antenna 2 and the reflection antenna 3 is set to be $\lambda/4$. The length of the reflection antenna 3 is set to be the same as the length of the reception antenna 2 in FIG. 4-(A), and is set to be greater than that of the reception antenna 2 in FIG. 4-(B). Similarly to the directional antenna, since the matching of the impedance changed due to the mutual operation when two antennas approach each other is taken into consideration, it is preferable that the antenna length or the distance between the antennas is slightly less than the dimension.

In the case of FIG. 4-(A), electromotive force is generated by a magnetic field of the THz wave incident on the reflection antenna 3, and an induced current flows. In this case, since the length of the reflection antenna 3 is the same as that of the reception antenna 2 and the reactance component is 0, the electromotive force and the induced current have the same phase, and the phase of the THz wave re-radiated from the reflection antenna by the induced current is the same as that of the incident THz wave. Thus, the THz wave incident on the reception antenna and the THz wave re-radiated from the reflection antenna 3 are shifted by a phase of $\pi/2$, as shown in FIG. 4-(A).

In the case of FIG. 4-(B), since the length of the reflection antenna 3 is greater than that of the reception antenna 2, the reflection antenna has an inductive reactance component, the phase of the induced current flowing due to the THz wave incident on the reflection antenna 3 is further delayed than that of the electromotive force by π/2. The phase of the THz wave re-radiated from the reflection antenna by the induced current is further delayed than that of the incident THz wave by π/2. The distance z2 between the reception antenna 2 and the reflection antenna 3 is set to be λ/4 (that is, equivalent to π/2 as the phase). Thus, since the THz wave incident on the reception antenna 2 and the THz wave re-radiated from the reflection antenna 3 have the same phase on the incident side of the reception antenna 2, these waves reinforce each other. Since these waves have reversed phases to each other, these waves weaken each other. As a result, the incident side has strong directivity.

It is possible to achieve the antenna structure in which the directional antenna has strong directivity by combining the above-described principles. Since the thickness of the antenna is thin, the distances z1 and z2 are the z-axis direction distances between the center positions of gravity of the antennas. Even though these distances are distances between facing front surfaces of the antennas, the same relationship is established, and the above-described effect is acquired.

Figure 7:
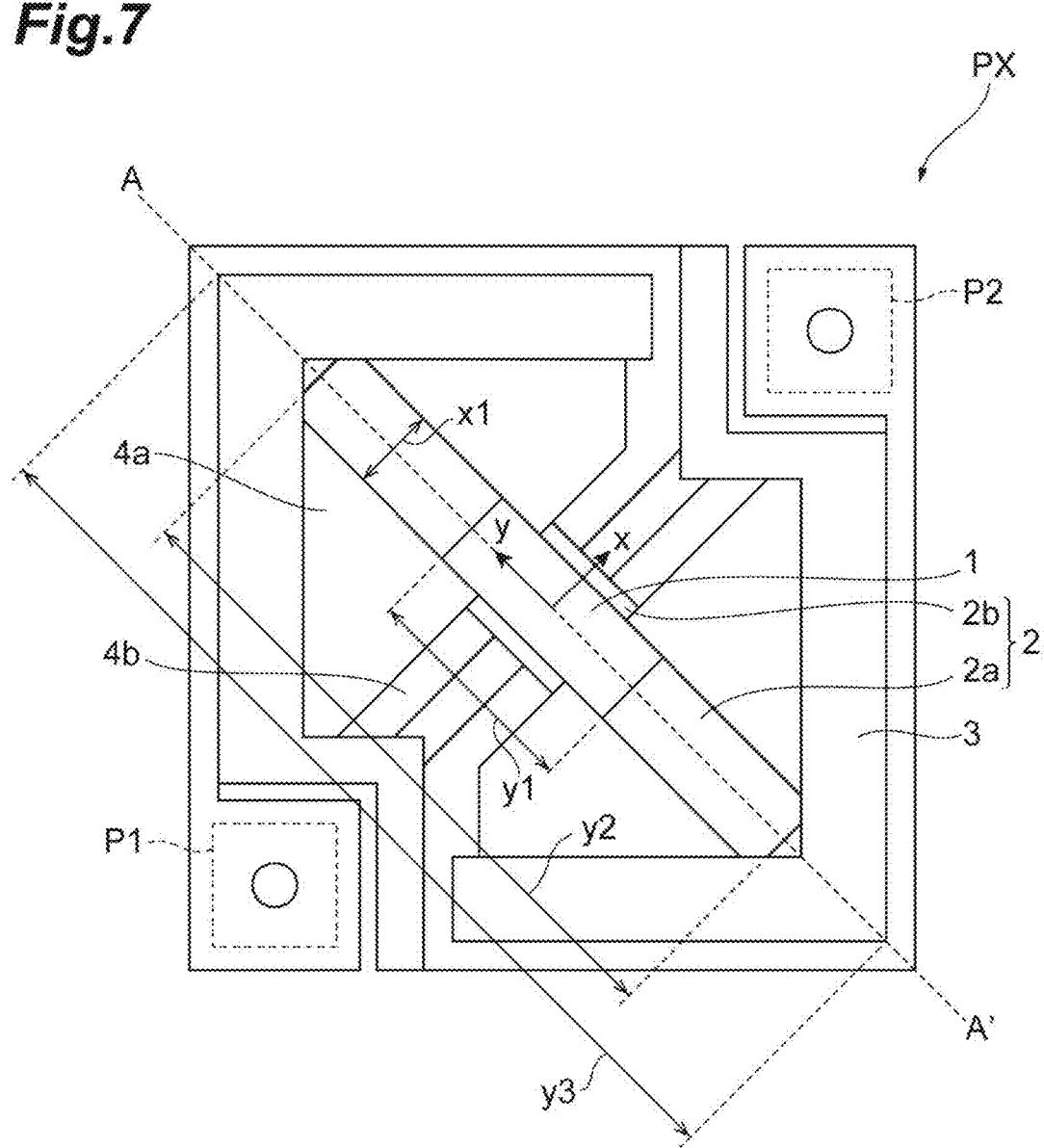
FIG. 7 is a plan view of the THz bolometer detector (except for a lid).

FIG. 5 is a diagram showing a specific sectional structure of the THz bolometer detector 100 according to the first embodiment, and shows a sectional structure taken along a diagonal line A-A' in FIG. 7. A basic structure is as described in FIG. 1, and thus, the detailed structure will be described.

The lid member 6 includes a silicon substrate 6b including the recess portion D1, and a depth d1 of the recess portion D1 of the silicon substrate 6b is set to be equal to greater than 10 μm and is equal to or less than 400 μm, preferably equal to or less than 300 μm, more preferably equal to or less than 200 μm, and even more preferably equal to or less than 100 μm. A thickness d2 of a peripheral portion of the silicon substrate 6b is equal to or greater than 200 μm and is equal to or less than 2 mm, and more preferably equal to or less than 1 mm. It is assumed that a distance between a lower surface of the bolometer 4 and an exposed front surface of a coating film 8 is d3. As an example, the dimensions are set such that d1=13.5 μm, d2=600 μm, and d3=2 μm.

A pressure lower than an atmospheric pressure is set within the enclosed space including the recess portion D1. The pressure lower than the atmospheric pressure is preferably vacuum (0.1 Pa or less), and thus, it is possible to perform detection having high environment tolerance with high sensitivity. Since the recess portion D1 is formed in the silicon substrate 6b, the silicon substrate 6b is likely to be deformed by a pressure difference. Here, the depth d1 of the recess portion D1 of the silicon substrate 6b is set to be within a shallow range as stated above and a substrate thickness is secured, and thus, the silicon substrate 6b can be prevented from being deformed. The thickness d2 of the peripheral portion is set to be within the above-described range, and thus, a thickness of a thin plate of the silicon substrate immediately under the recess portion is prevented from being excessively thick. As a result, it is possible to suppress high attenuation of the THz wave. In a case where the substrate thickness is equal to or greater than a lower limit and the depth of the recess portion is equal to or less than an upper limit, there are some cases where the deformation of the substrate is suppressed but the substrate is deformed out of the range. In order to reduce the pressure of the enclosed space, the lid member and the support substrate may be attached to each other under a depressurized environment (vacuum).

An anti-reflection film 6c is formed on a surface opposite to the recess portion D1 of the silicon substrate 6b, and an insulation film 6a is formed on an internal surface of the recess portion D1 of the silicon substrate 6b. A material of the anti-reflection film 6c is a $SiO_2$ or poly(para-xylylene) (parylene (registered trademark)), a material of the insulation film 6a is $SiO_2$ or poly(para-xylylene), and resistivity of the silicon substrate 6b is set to be equal to or greater than 1 kΩcm. In this case, since the reflection of the THz wave is suppressed by the anti-reflection film and the amount of impurities is small within the substrate, the attenuation of the THz wave is low, and thus, the THz wave can be sufficiently incident on the directional antenna 1.

The sealing member 7 includes two layers such as an Au layer 7a and an AuSn layer 7b. The sealing member 7 is provided between the insulation film 6a and the coating film 8 made of an insulator. A front surface of the support substrate 5 is coated with the coating film 8, and a front surface of the reflection antenna 3 is also coated with the coating film 8. A protecting insulation film 5e is formed on a rear surface of the semiconductor substrate 5a constituting the support substrate 5.

Wiring 10 that is electrically connected to both ends of the bolometer 4 is connected to the insulation film 5c on the front surface of the support substrate 5, and the wiring 10 is connected to the read circuit 5b. In a case where a position of the read circuit 5b is provided immediately under the reflection antenna 3, the read circuit 5b is protected from the electromagnetic wave. The wiring 10 may be connected to a circuit positioned outside the lid member if necessary.

The directional antenna 1 is made of metal such as aluminum, and is fixed to the bottom surface of the recess portion D1.

The reception antenna 2 is made of metal such as aluminum, and is fixed to the bolometer 4.

The reflection antenna 3 is a reflection plate, and is made of metal such as aluminum.

The bolometer 4 includes a membrane 4a made of an insulator such as $SiO_2$ or SiNx, pieces of wiring 4b made of metal (silicide including W, Ti, or Mo) having a high melting point formed on the membrane 4a, a resistor layer 4c that electrically connects separation areas of the pieces of wiring 4b and coats the membrane 4a and the wiring 4b, and a protection layer 4d made of an insulator ($SiO_2$ or SiNx) that coats the resistor layer 4c. The reception antenna 2 is fixed to the protection layer 4d. The resistor layer 4c is made of amorphous silicon.

Figure 6:
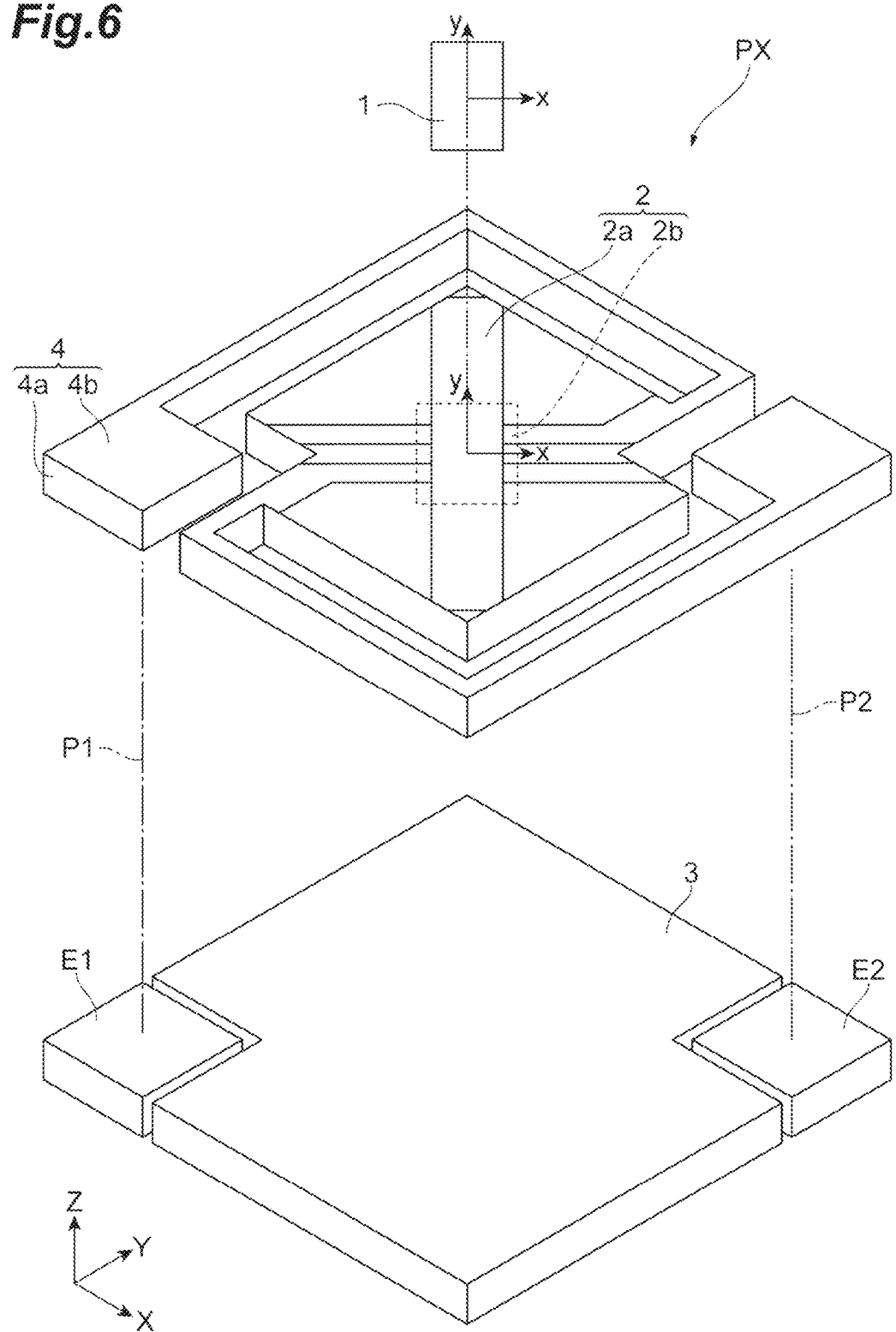
FIG. 6 is a perspective view showing an exploded THz bolometer detector.
Figure 8:
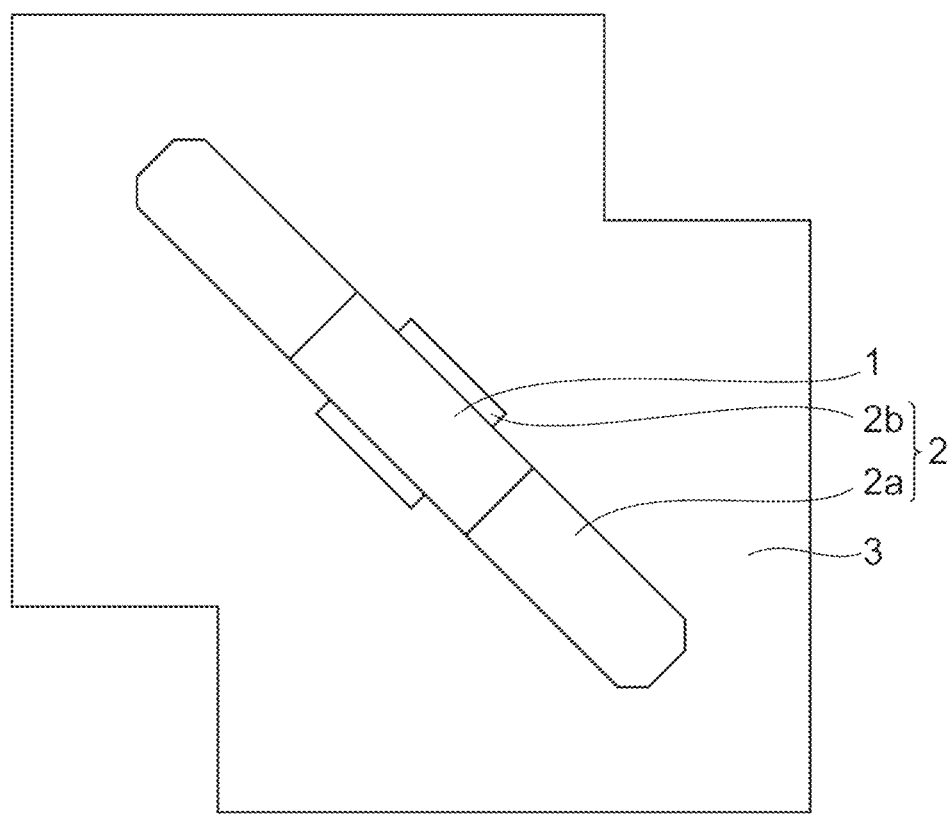
FIG. 8 is a plan view of an antenna group of the THz bolometer detector.

FIG. 6 is a perspective view showing an exploded THz bolometer detector, FIG. 7 is a plan view of the THz bolometer detector (except for the lid), and FIG. 8 is a plan view of the antenna group of the THz bolometer detector.

The reflection antenna 3 is a rectangular reflection plate that is widened in an XY plane in an XYZ orthogonal coordinate system. Two corners of the reflection antenna are cut, and electrode pads E1 and E2 are provided in the cut positions. Electrode plugs P1 and P2 are connected to the electrode pads E1 and E2, respectively, and are electrically connected to the pieces of wiring 4b formed on an upper surface of the membrane 4a. A circular contact hole is formed in the membrane 4a, and the electrode plugs P1 and P2 are connected to both ends of the pieces of wiring 4b through the contact hole.

The membrane 4a made of the insulator includes a beam portion that extends along a circumference of the reflection antenna 3, and a central portion that is continuously connected to the beam portion and has a shape in which two corners are cut in a quadrilateral shape in plan view. A pair of pieces of wiring 4b is provided on the membrane 4a, extends along a diagonal line (x-axis direction) of the central portion of the membrane 4a, and is separated in the y-axis direction. The resistor layer 4c is positioned between the separated pieces of wiring, and is not shown in FIG. 6 for the sake of convenience in the description. The longitudinal direction (x-axis direction) of the wiring 4b in the central portion of the membrane is perpendicular to the longitudinal direction (y-axis direction) of the reception antenna 2. The longitudinal directions (y-axis directions) of the reception antenna 2 and the directional antenna 1 match each other.

As stated above, the dimension y1 of the directional antenna 1, the dimension y2 of the reception antenna 2, and the dimension y3 along the diagonal line of the reflection antenna 3 having a quadrilateral shape in which two corners are cut satisfy y1<y2<y3 (see FIG. 7). Both planar shapes of the directional antenna 1 and the pair of linear antennas constituting the reception antenna 2 are substantially rectangular shapes, and dimensions x1 thereof in the width direction are the same.

For example, the dimensions may be set such that y1=14 μm, y2=43 μm, and x1=5.4 μm, and preferred values of y1, y2, and x1 capable of acquiring favorable characteristics are 10 μm≤y1≤100 μm, 20 μmm≤y2≤250 m, and x1≤10 μm. An energy line (light or electromagnetic wave) incident on the THz bolometer detector may have a frequency of 0.5 THz to 3 THz.

The reflection antenna 3 has the same pattern as that of the membrane 4a of the bolometer 4 in plan view. The central portion of the membrane 4a completely overlaps the reflection antenna 3 in plan view. A diagonal length of the reflection antenna 3 overlapping the reception antenna 2 in plan view is greater than a length of the reception antenna 2. As stated above, since the reflection antenna 3 has the same pattern as that of the membrane, the reception efficiency of the THz wave is improved due to an antenna effect. Thus, radiant heat radiated from the membrane warmed by generated heat is reflected from the reflection plate, and is efficiently absorbed to the membrane again. The reflection antenna 3 may have the same shape as that of the reception antenna 2, and may have a shape such as a rectangular shape in which the reflection antenna is longer than the reception antenna.

In addition to the above-described structure, a plurality of antennas may be provided on the membrane, the directional antennas may be provided in multiple stages in order to improve sensitivity, it may be easy to perform impedance matching by folding the reception antenna and using the bent reception antenna as the dipole antenna may be considered, a configuration in which the reception antenna is used as a meander type dipole antenna and a length thereof is less than a half-wave linear dipole antenna may be provided, or a modification such as a structure in which bow-tie antennas are employed and these bow-tie antennas layered may be considered.

Figure 11:
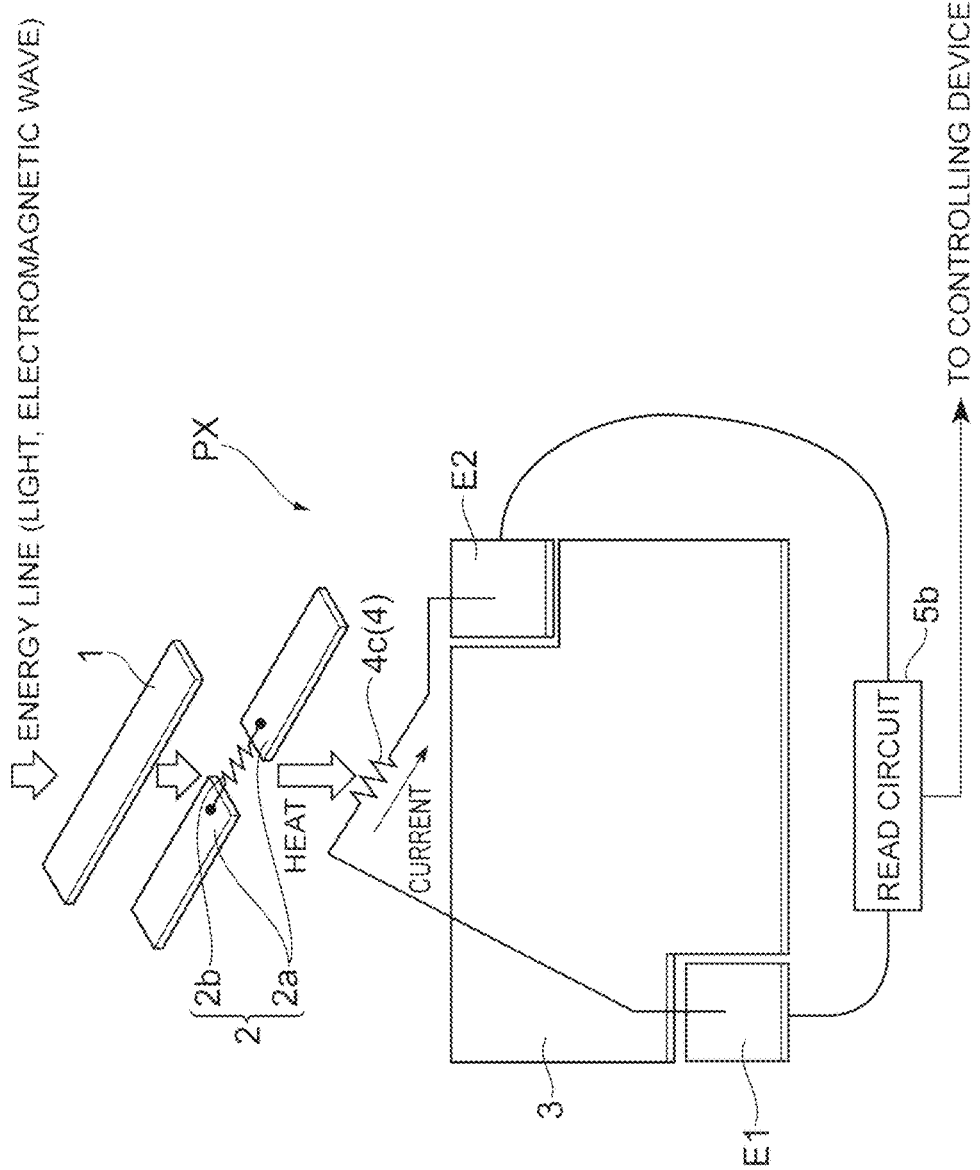
FIG. 11 is a diagram showing an operation principle of the THz bolometer detector.

FIG. 11 is a diagram showing an operation principle of the THz bolometer detector.

The energy line (light or electromagnetic wave) is received by the reception antenna 2 through the directional antenna 1, and a part thereof is reflected from the reflection antenna 3 and is received by the reception antenna 2. The energy line is the THz wave. The reception antenna 2 includes the dipole antenna 2a including the pair of linear antennas and the resistor 2b provided in the gap between the antennas. A current flows to the resistor 2b depending on intensity of the received energy, and heat is generated.

The heat generated in the resistor 2b is transferred to the resistor layer 4c (bolometer 4) provided near the resistor 2b. Both ends of the resistor layer 4c are electrically connected to the electrode pads E1 and E2, respectively, and magnitude of the current flowing in the resistor layer 4c is changed by the resistance value of the resistor layer 4c. Since the resistance value of the resistor layer 4c depends on a temperature, the magnitude of the current flowing in the resistor layer 4c is changed depending on the intensity of the received energy. The current flowing in the resistor layer 4c is detected by the read circuit 5b, and a detection output is input to a controlling device.

The directional antenna 1, the reception antenna 2, the reflection antenna 3, and the resistor layer 4c constitute a single pixel PX. In the above-described example, an example in which one pixel PX is included in one capturing area and one reception antenna is provided in one pixel is illustrated. However, a plurality of pixels may be included in one capturing area, and a plurality of reception antennas may be provided within one pixel. Reception characteristics (frequency or polarization orientation) of the antennas may be different from each other, and thus, outputs from pixels including these antennas may be acquired, or a difference between pixel outputs may be calculated. Hereinafter, the details thereof will be described.

Figure 12:
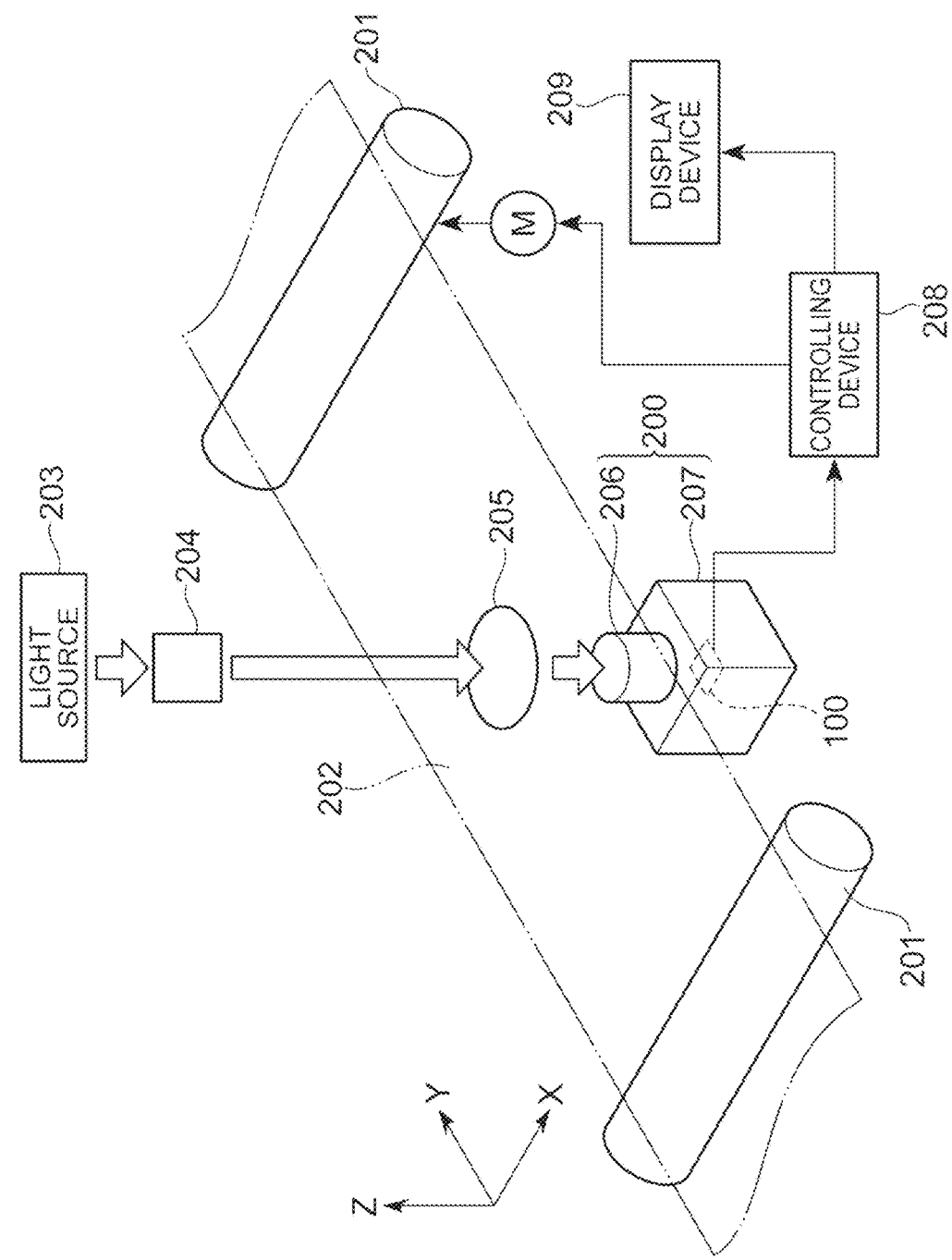
FIG. 12 is a perspective view of a testing device using the THz bolometer detector.

FIG. 12 is a perspective view of a testing device using the THz bolometer detector.

A transport belt 202 is provided on a plurality of rotating rollers 201, and the rotating rollers 201 are rotated by a motor M. A belt conveyor is constituted by the motor M, the rotating rollers 201, and the transport belt 202, and an object 205 placed on the transport belt 202 may be transported along the Y-axis direction by driving the motor M.

A magnifying lens 204 and a light source 203 for irradiating the object 205 with the THz wave as the energy line are provided above the transport belt 202. The light source 203 is not particularly limited as long as the light source generates the energy line as the THz wave, and a quantum cascade laser (QCL) or a gas laser may be used. The quantum cascade laser is a semiconductor laser using optical transitions between quantum levels (subbands) formed in a semiconductor quantum well, and may output laser light in a THz region. The laser light emitted from the light source 203 proceeds along the Z-axis direction, and is incident on the object 205 after a diameter thereof is expanded by the magnifying lens 204. The object 205 is an object of nondestructive testing, and includes various products.

The transport belt 202 is made of a material through which the laser light transmits or has a hole through which the laser light passes. The laser light that transmits through the object 205 or passes or transmits through the transport belt 202 is incident on a nondestructive testing camera 200. The nondestructive testing camera 200 includes a capturing lens 206, and the THz bolometer detector 100 accommodated in a box 207. The laser light incident on the nondestructive testing camera 200 forms an image by the capturing lens 206, and is incident on the THz bolometer detector 100.

The capturing lens 206 concentrates the incident laser light or forms an image on the reception antenna 2 of the THz bolometer detector 100. A laser incident on the THz bolometer detector 100 outputs a current to a controlling device 208 depending on incident intensity of the laser light incident on the THz bolometer detector, as a detection result. The controlling device 208 may display the detection result by the THz bolometer detector 100 on a display device 209.

The controlling device 208 controls the motor M of the belt conveyor, and may move the transport belt 202, may move the object 205 up to a position above the nondestructive testing camera 200, and may stop the object 205 in a position above the nondestructive testing camera 200. The controlling device 208 controls emission of the light source 203, and may control the light source 203 to irradiate the object 205 with the laser light when the object 205 is stopped.

As stated above, the THz bolometer detector 100 may be configured such that a plurality of pixels is included in one capturing area and a plurality of reception antennas is included in one pixel. Hereinafter, the details thereof will be described.

Figure 13:
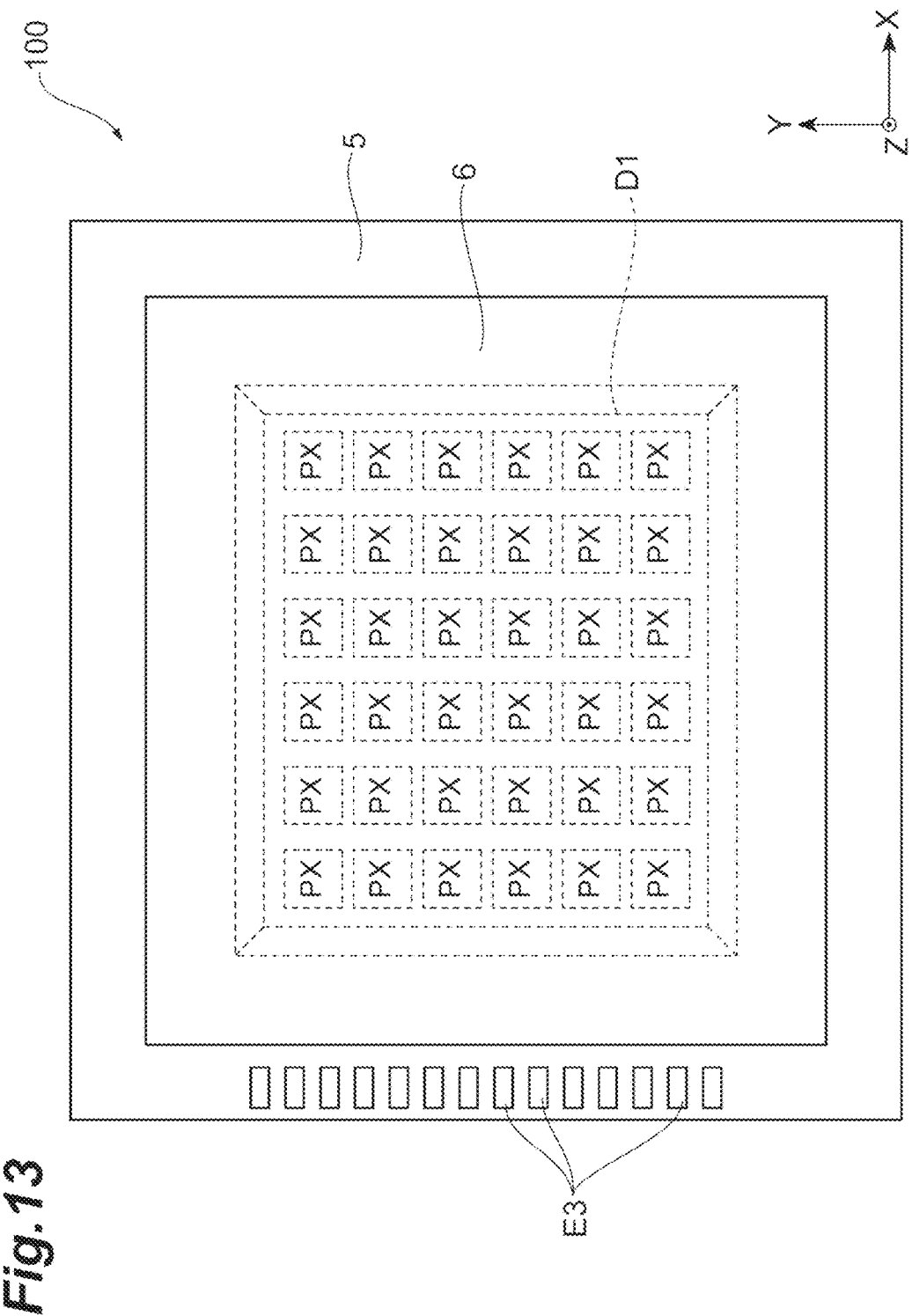
FIG. 13 is a plan view of a THz bolometer detector according to a second embodiment.

FIG. 13 is a plan view of a THz bolometer detector 100 according to a second embodiment.

The THz bolometer detector 100 includes a lid member 6 including a recess portion D1, and a support substrate 5 that is coated with the lid member 6 and defines an enclosed space including the recess portion D1 in cooperation with the lid member 6. The THz bolometer detector 100 according to the second embodiment is different from that of the first embodiment that a plurality of pixels PX arranged in a matrix shape is provided within the enclosed space and signal extraction electrodes E3 are provided on the support substrate 5, and other configurations thereof are the same. Although the pixels PX are arrayed along the X-axis direction and the Y-axis direction, a pixel arrangement direction is not limited thereto, and various arrays such as a one-dimensional array or a honeycomb array may be used. The number of pixels arranged in one capturing area (within the enclosed space) is not limited to the drawing.

Each of the pixels PX includes a directional antenna 1, a reception antenna 2, a reflection antenna 3, and a bolometer 4, and the pixels may respectively output currents in response to the incident THz waves. The currents output from the pixels PX may be extracted to the outside through the signal extraction electrodes.

Figure 14:
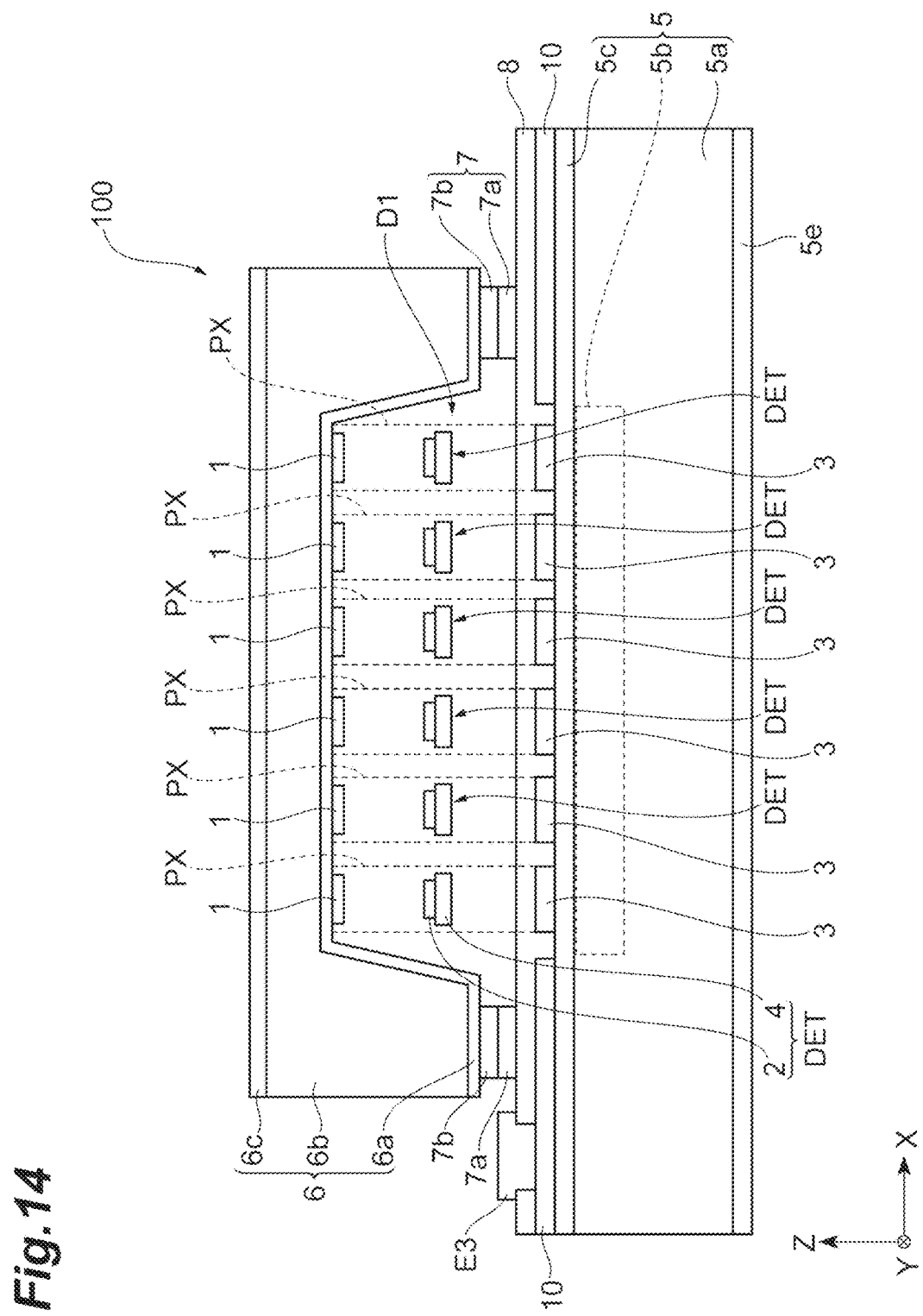
FIG. 14 is a diagram showing a sectional structure of the THz bolometer detector according to the second embodiment.

FIG. 14 is a diagram showing a sectional structure of the THz bolometer detector 100 according to the second embodiment.

As stated above, differences between the THz bolometer detector 100 according to the second embodiment and the THz bolometer detector 100 according to the first embodiment shown in FIG. 5 are only the number of pixels and whether or not there is the plurality of signal extraction electrodes E3. Accordingly, the THz bolometer detector 100 includes the support substrate 5, the lid member 6 that is attached to the support substrate 5 through a sealing member 7, and the plurality of pixels PX arranged in the enclosed space defined between the recess portion D1 of the lid member 6 and the support substrate 5.

Although the pixel PX includes the directional antenna 1, the reception antenna 2, the reflection antenna 3, and the bolometer 4, if a structure including the reception antenna 2 and the bolometer 4 is used as a detection unit DET, the THz bolometer detector 100 includes a plurality of detection units DET. The structures of the directional antenna 1, the reflection antenna 3, the reception antenna 2, and the bolometer 4 are the same as the structures of the directional antenna 1, the reflection antenna 3, the reception antenna 2, and the bolometer 4 shown in FIGS. 5 to 8.

An output of the bolometer 4 is read by a read circuit 5b formed on a silicon substrate which is a semiconductor substrate 5a, and is read to the outside through wiring 10 and the electrodes E3 connected to the read circuit.

Surfaces of the reflection antennas 3 and the wiring 10 are coated with a coating film 8, and the wiring 10 extends up to the outside of the lid member 6. The coating film 8 includes a plurality of openings outside the lid member, and the signal extraction electrodes E3 are arranged within these openings. That is, the signal extraction electrodes E3 are in contact with the surface of the wiring 10 and are electrically connected to the wiring 10, and the wiring 10 is connected to the output of each of the pixels PX through the read circuit 5b. The read circuit 5b includes an amplifier, the outputs from the plurality of pixels PX are sequentially input to the amplifiers, are amplified, and are extracted to the outside.

Other configurations and operations in the second embodiment are the same as those in the first embodiment.

Figure 15:
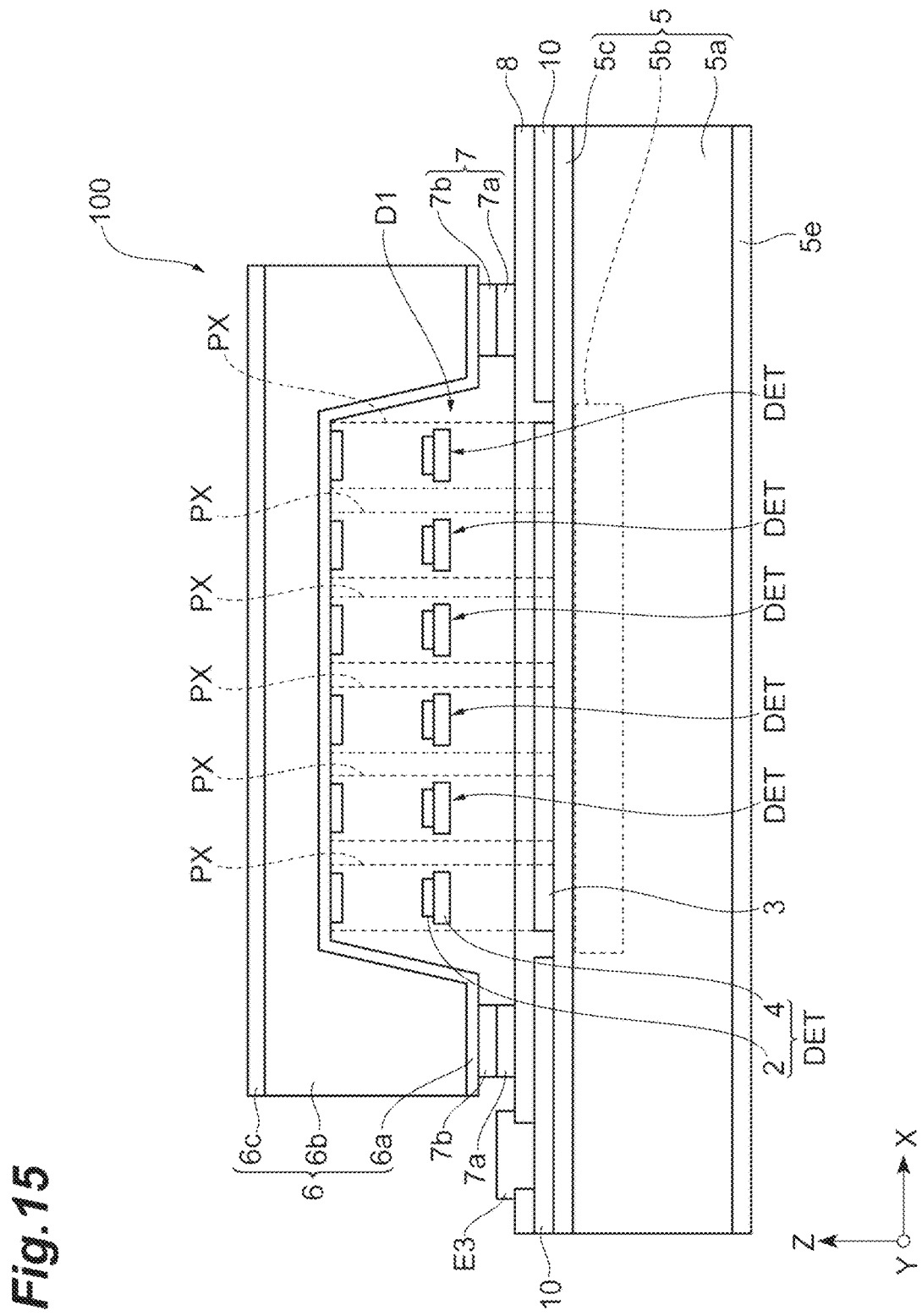
FIG. 15 is a diagram showing a sectional structure of a THz bolometer detector according to a modification example.

FIG. 15 is a diagram showing a sectional structure of a THz bolometer detector 100 according to a modification example.

Although the reflection antennas 3 in the individual pixels PX are separated from each other in the THz bolometer detector 100 shown in FIG. 14, the reflection antennas 3 are not separated from each other and extend so as to traverse the pixels PX in the modification example shown in FIG. 15. As long as the reflection antenna 3 has a reflection function of the incident THz wave, a certain effect can be obtained even in such a case.

Figure 16:
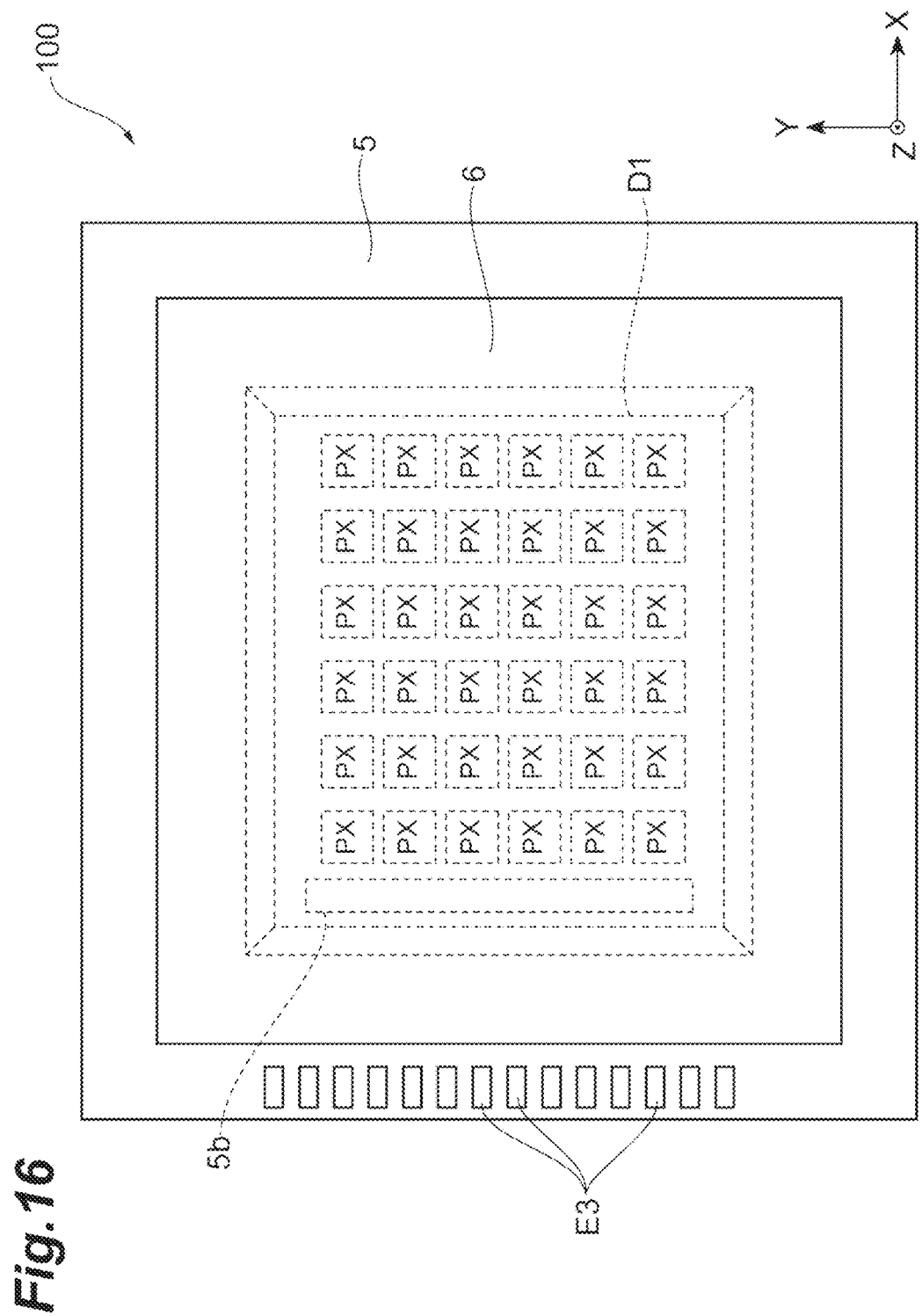
FIG. 16 is a plan view of a THz bolometer detector according to a third embodiment.
Figure 17:
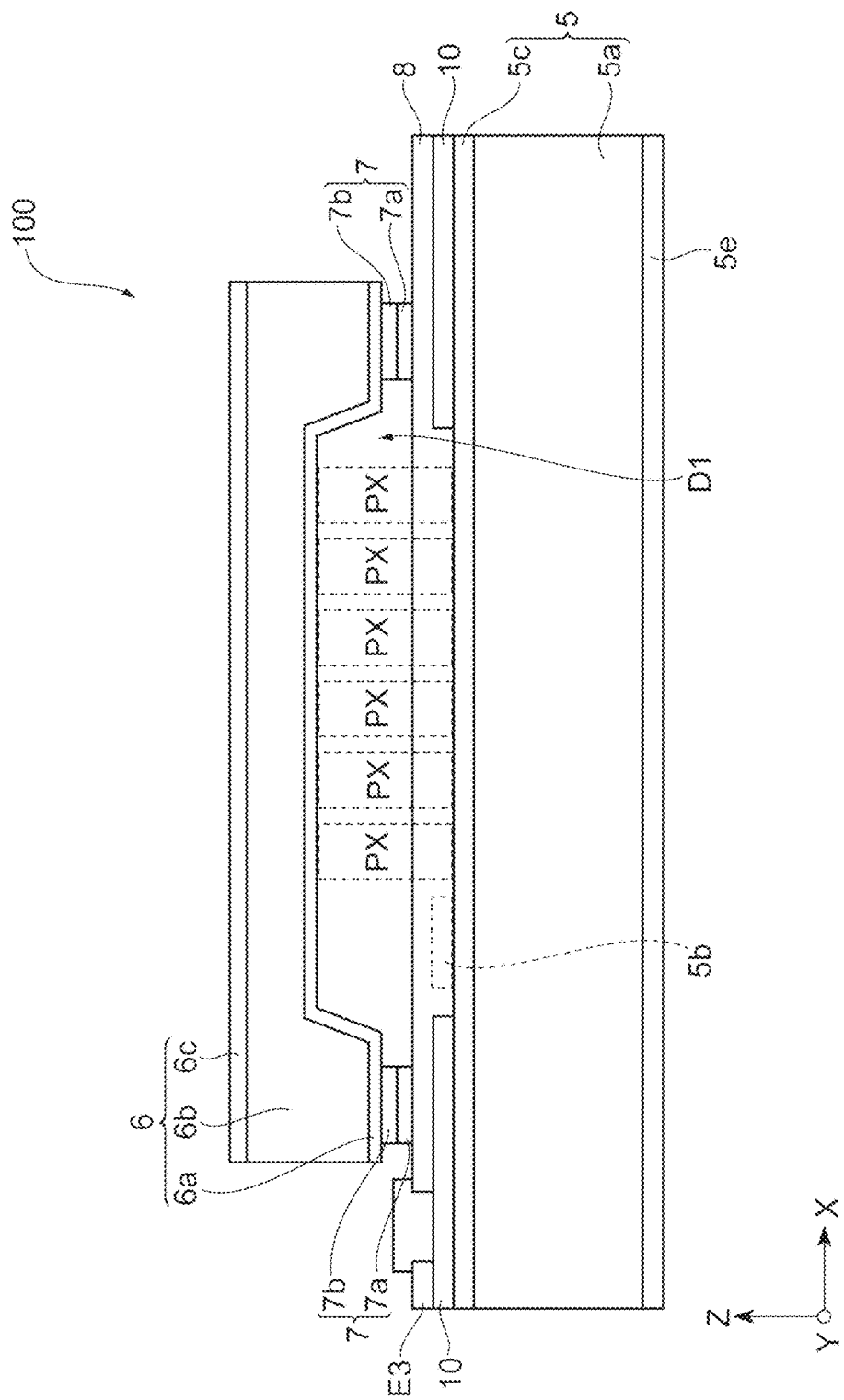
FIG. 17 is a diagram showing a sectional structure of the THz bolometer detector according to the third embodiment.

FIG. 16 is a plan view of a THz bolometer detector according to a third embodiment, and FIG. 17 is a diagram showing a sectional structure of the THz bolometer detector according to the third embodiment.

A difference between the THz bolometer detector 100 according to the third embodiment and the THz bolometer detector 100 according to the second embodiment shown in FIGS. 13 and 14 is only a position of the read circuit 5b, and other structures and operation effects are the same. The read circuit 5b according to the third embodiment is provided in an area between a capturing area including the plurality of pixels Px and the electrodes E3.

The read circuit 5b is formed separately from the semiconductor substrate 5a made of silicon. That is, an integrated circuit chip including the read circuit 5b is provided on an insulation film 5c that coats the semiconductor substrate 5a. The read circuit 5b may be formed within the semiconductor substrate 5a.

Figure 18:
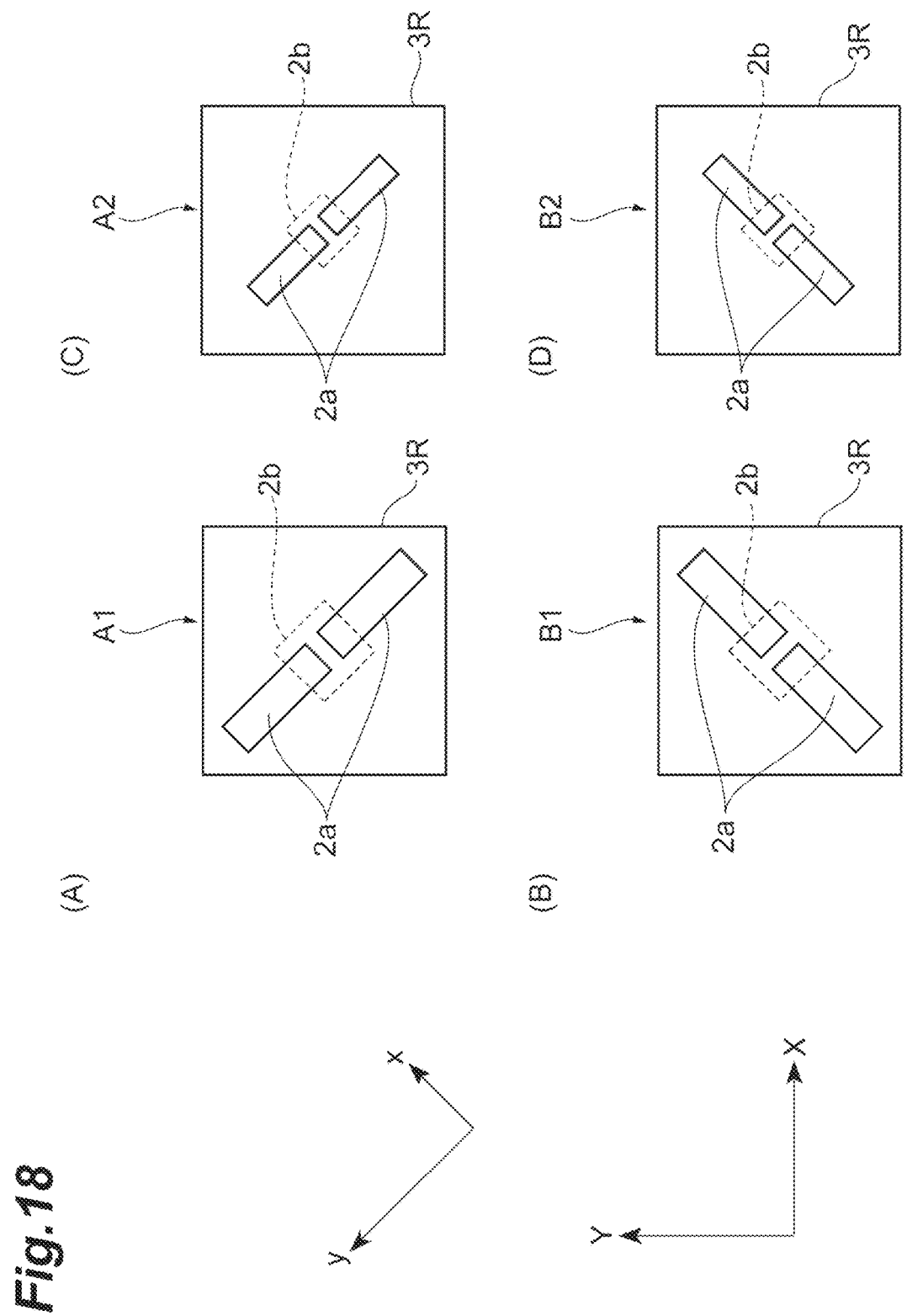
FIG. 18 shows plan views of various types of unit sensors.

FIG. 18 shows plan views of various types of unit sensors.

The unit sensor has the same basic structure as that of the pixel PX shown in FIG. 6 or 11, and includes a directional antenna 1 (not shown in FIG. 18), a reception antenna 2, a reflection antenna 3R, and a bolometer 4 (not shown in FIG. 18) shown in FIG. 6 or 11. Conditions in which the respective antennas satisfy are the same as those described above, and the longitudinal directions (y-axis directions) of the directional antenna 1 and the reception antenna 2 match each other. Although a shape of the reflection antenna 3R is simplified as a square, two neighboring sides constituting the square extend so as to match the X-axis direction and the Y-axis direction.

The longitudinal direction (y-axis direction) of the reception antenna 2 matches a polarization direction of a THz wave to be received, and the length thereof corresponds to a frequency to be sensitive. Accordingly, it is possible to detect the THz wave having various polarization or frequencies by changing the longitudinal direction and the length of the reception antenna 2 (directional antenna 1).

(A) of FIG. 18 shows a unit sensor A1, (B) shows a unit sensor B1, (C) shows a unit sensor A2, and (D) shows a unit sensor B2. The xy coordinate system is acquired by rotating the XY coordinate system by 45°.

The unit sensor A1 includes the reception antenna 2 (the paired dipole antenna 2a and resistor 2b), and the longitudinal direction of the reception antenna 2 matches the y-axis direction. The unit sensor B1 includes the reception antenna 2 (the paired dipole antenna 2a and resistor 2b), and the longitudinal direction of the reception antenna 2 matches the x-axis direction. That is, the longitudinal direction of the reception antenna 2 of the unit sensor A1 and the longitudinal direction of the reception antenna 2 of the unit sensor B1 are perpendicular to each other, and the lengths in the longitudinal direction are the same. Accordingly, the unit sensor A1 and the unit sensor B1 can receive the THz waves having the same frequency and polarization orientations perpendicular to each other.

The unit sensor A2 includes the reception antenna 2 (the paired dipole antenna 2a and resistor 2b), and the longitudinal direction of the reception antenna 2 matches the y-axis direction. The unit sensor B2 includes the reception antenna 2 (the paired dipole antenna 2a and resistor 2b), and the longitudinal direction of the reception antenna 2 matches the x-axis direction. The longitudinal direction of the reception antenna 2 of the unit sensor A2 and the longitudinal direction of the reception antenna 2 of the unit sensor B2 are perpendicular to each other, and the lengths in the longitudinal direction are the same.

The longitudinal direction of the reception antenna 2 of the unit sensor A1 and the longitudinal direction of the reception antenna 2 of the unit sensor A2 match each other, and the lengths in the longitudinal direction are different from each other. Accordingly, the unit sensor A1 and the unit sensor A2 can receive the THz waves having different frequencies from each other and the same polarization orientation.

The longitudinal direction of the reception antenna 2 of the unit sensor A1 and the longitudinal direction of the reception antenna 2 of the unit sensor B2 are perpendicular to each other, and the lengths in the longitudinal direction are different from each other. Accordingly, the unit sensor A1 and the unit sensor B2 can receive the THz waves having different frequencies from each other and different polarization orientations from each other.

It is possible to detect the THz waves depending on reception characteristics of the unit sensors by arranging the plurality of unit sensors in the capturing area.

Figure 19:
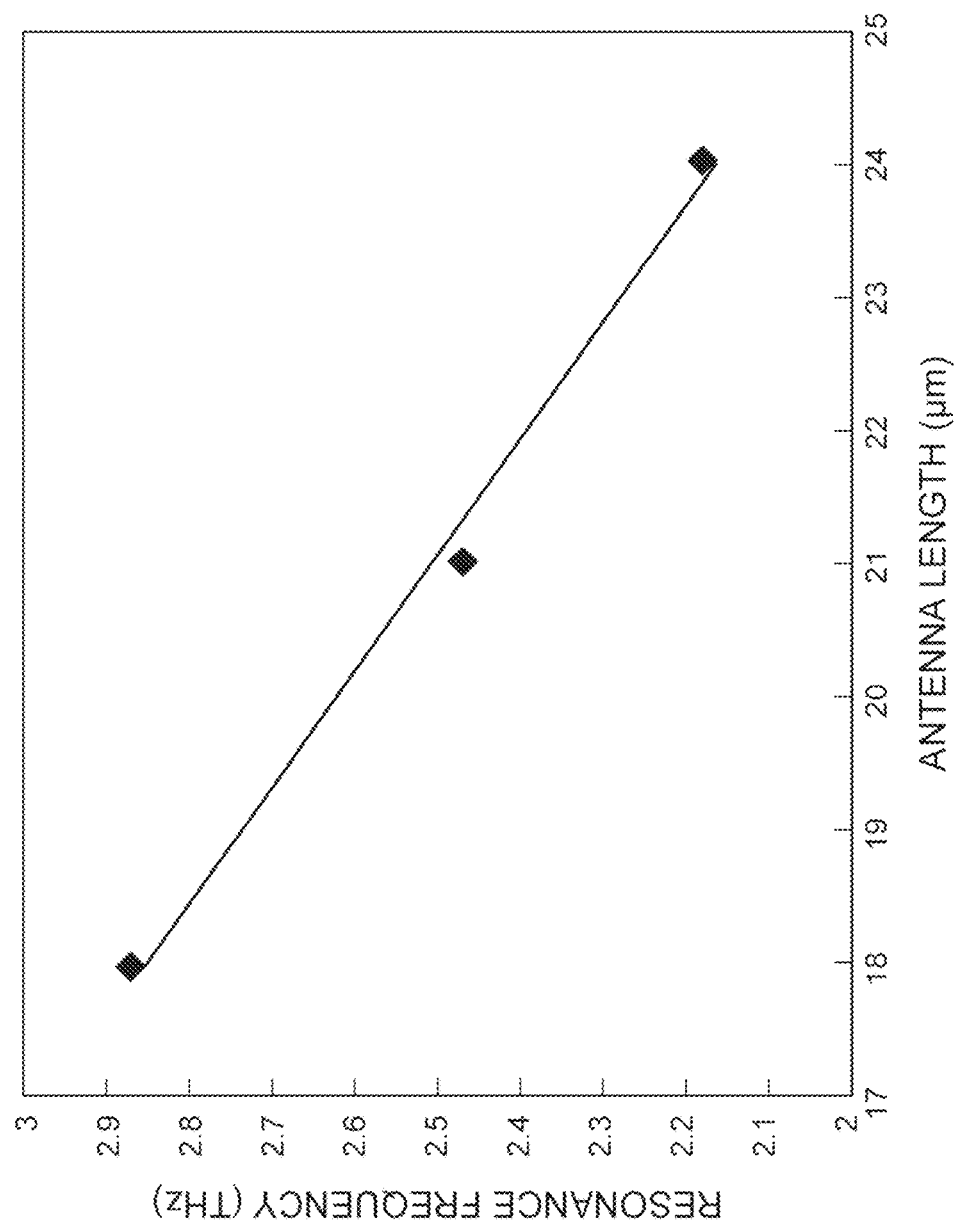
FIG. 19 is a graph showing the relationship between an antenna length (μm) and a resonance frequency (THz).

FIG. 19 is a graph showing the relationship between an antenna length (μm) of the dipole antenna 2a constituting the reception antenna in the longitudinal direction and a resonance frequency (THz).

As the antenna length is long, the resonance frequency (THz) in the reception antenna is reduced. Specifically, if a linear approximation is performed on a change of a resonance frequency f (THz) with respect to an antenna length y2 (μm), an expression of $f=-0.115 \times y2 + 4.9217$ is satisfied. That is, when the antenna length y2 is 18 (μm), the resonance frequency f is 2.86 (THz), and when the antenna length y2 is 24 (μm), the resonance frequency f is 2.16 (THz).

As mentioned above, in the THz bolometer detector according to the embodiment, it is possible to selectively receive desired THz waves by changing the antenna length of the reception antenna.

The pixel PX includes the unit sensor and is positioned within the enclosed space of the recess portion of the lid member. An area within the recess portion in which the unit sensors are arranged defines a capturing area IMG in plan view.

Figure 20:
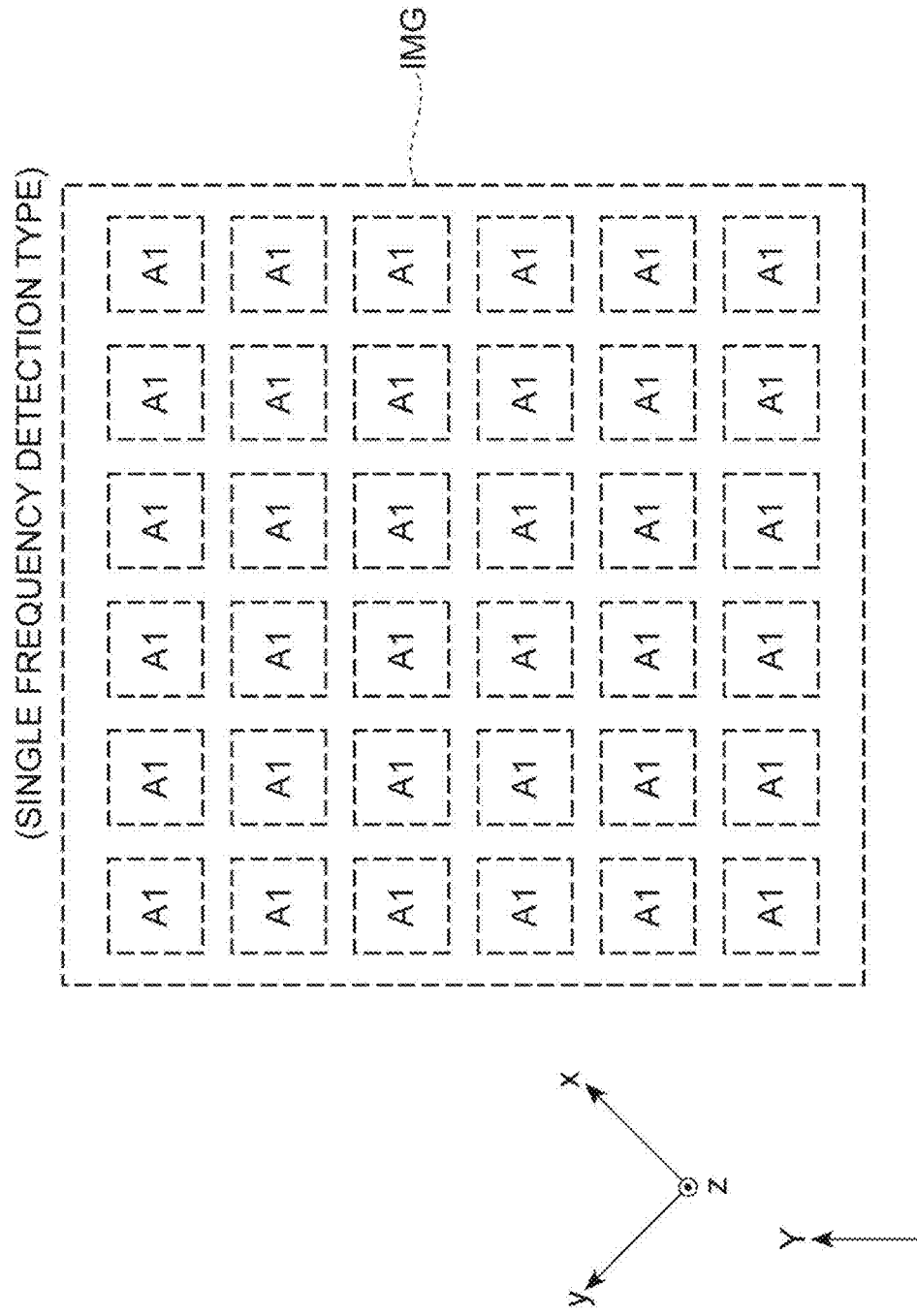
FIG. 20 is a diagram showing an arrangement example of unit sensors (pixels) in a capturing area IMG.

FIG. 20 is a diagram showing an arrangement example (single frequency detection type) of the unit sensors (pixels) in the capturing area IMG.

The present example is an example in which the unit sensors A1 are arranged in matrix shape along the X axis and the Y axis in the THz bolometer detector according to the above-described embodiment. Since only one type of unit sensors A1 are arranged in the capturing area IMG, it is possible to detect THz waves having a single frequency in the THz bolometer detector.

FIG. 21 is a diagram showing an arrangement example (multiple frequency detection type) of the unit sensors (pixels) in the capturing area IMG.

The present example is an example in which the unit sensors A1 and the unit sensors A2 are alternately arranged along the X axis and are alternately arranged along the Y axis in the THz bolometer detector according to the above-described embodiment. Since two types of unit sensors A1 and unit sensors A2 having sensitivity to different frequencies are arranged in the capturing area IMG, it is possible to detect THz waves having two kinds of frequencies in the THz bolometer detector. Three or more kinds of unit sensors having sensitivity to different frequencies may be arranged, and in this case, it is possible to detect THz waves having three or more kinds of frequencies.

FIG. 22 is a diagram showing an arrangement example (multiple polarization detection type) of the unit sensors (pixels) in the capturing area IMG.

The present example is an example in which the unit sensors A1 and the unit sensors B1 are alternately arranged along the X axis and are alternately arranged along the Y axis in the THz bolometer detector according to the above-described embodiment. Since two types of unit sensors A1 and unit sensors B1 having sensitivity to polarizations having different orientations are arranged in the capturing area IMG, it is possible to detect THz waves having two kinds of polarizations in the THz bolometer detector. Three or more types of unit sensors having sensitivity to different polarizations may be arranged, and in this case, it is possible to detect THz waves having three or more kinds of polarizations.

Figure 23:
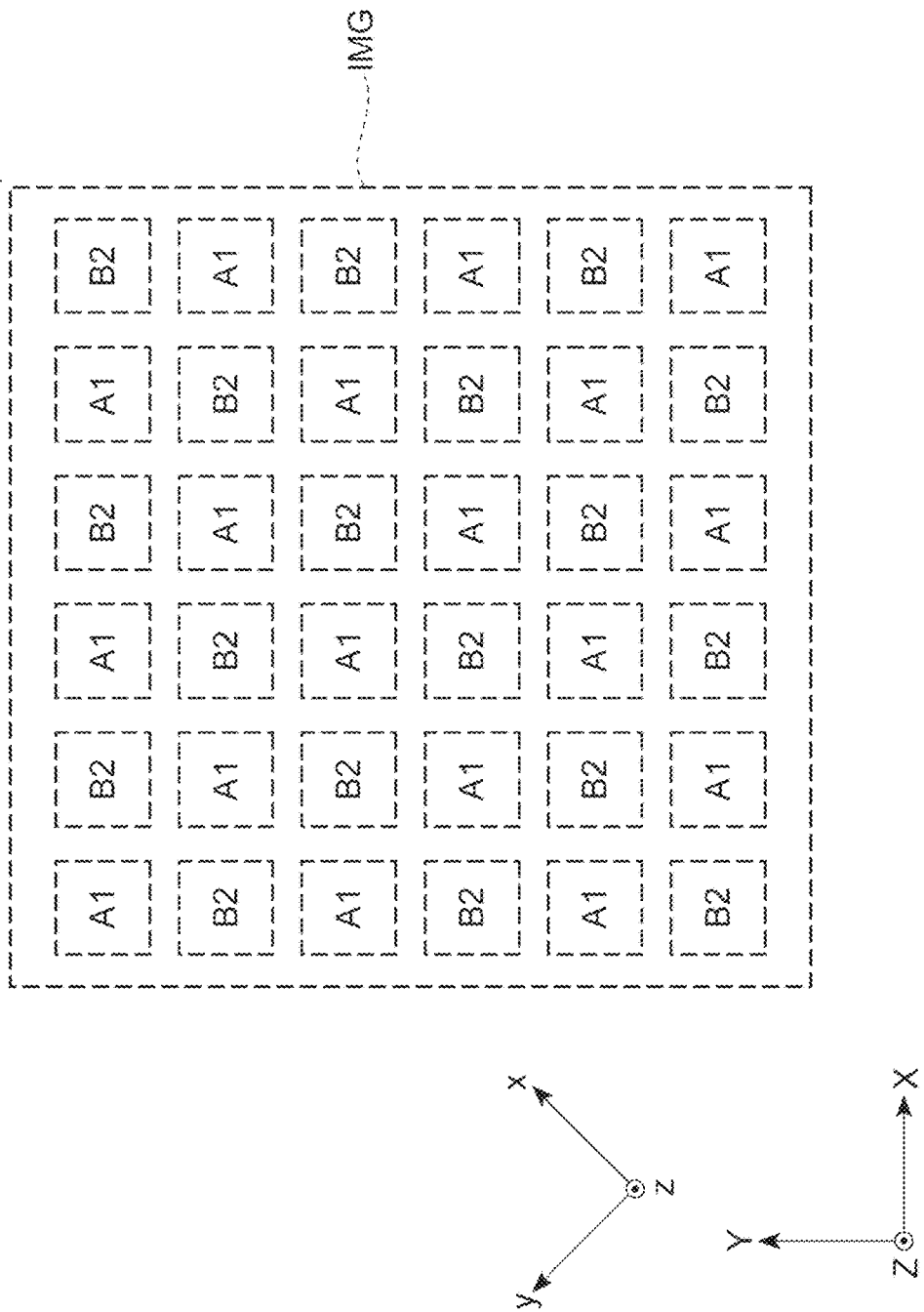
FIG. 23 is a diagram showing an arrangement example of the unit sensors (pixels) in the capturing area IMG.

FIG. 23 is a diagram showing an arrangement example (detection type in a case where both frequencies and polarizations are different) of the unit sensors (pixels) in the capturing area IMG.

The present example is an example in which the unit sensors A1 and the unit sensors B2 are alternately arranged along the X axis and are alternately arranged along the Y axis in the THz bolometer detector according to the above-described embodiment. Since two types of unit sensors A1 and unit sensors B2 having sensitivity to THz waves of which both frequencies and polarizations are different are arranged in the capturing area IMG, it is possible to detect two kinds of THz waves in the THz bolometer detector. Three or more types of unit sensors having sensitivity to THz waves of which frequencies and polarization orientations are different may be arranged, and in this case, it is possible to detect three or more kinds of THz waves.

Figure 24:
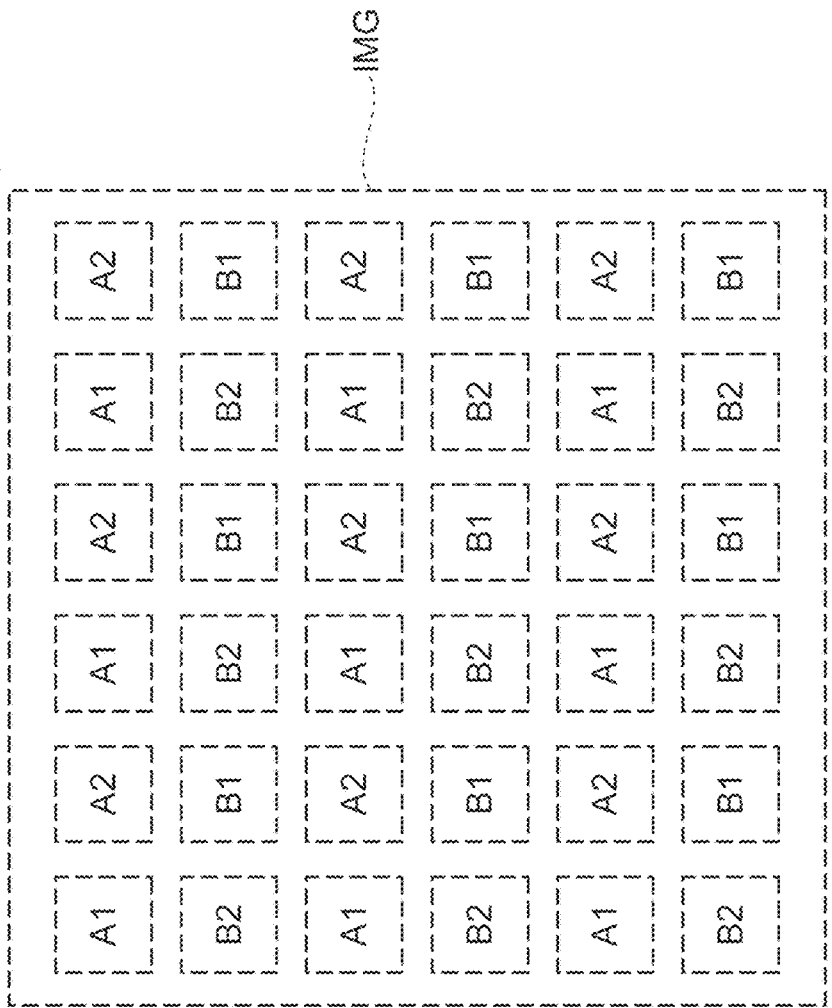
FIG. 24 is a diagram showing an arrangement example of the unit sensors (pixels) in the capturing area IMG.

FIG. 24 is a diagram showing an arrangement example (multiple frequency and multiple polarization detection type) of the unit sensors (pixels) in the capturing area IMG.

The present example is an example in which the unit sensors A1 and the unit sensors A2 are alternately arranged along the X axis, the unit sensors B1 and the unit sensors B2 are alternately arranged along the X axis, the unit sensors A1 and the unit sensors B2 are alternately arranged along the Y axis, and the unit sensors A2 and the unit sensors B1 are alternately arranged along the Y axis in the THz bolometer detector according to the above-described embodiment.

Since the unit sensors A1, A2, B1, and B2 having sensitivity to four kinds of THz waves are arranged in the capturing area IMG, it is possible to detect four kinds of THz waves in the THz bolometer detector. That is, two arbitrary unit sensors selected from the unit sensors A1, A2, B1, and B2 may divide the kind of the THz wave capable of being detected into four kinds of THz waves, which satisfy any relation of (1) a relationship when the frequencies are different and the polarization orientations are the same (relationship between A1 and A2 or between B1 and B2), (2) a relationship when the frequencies are the same and the polarization orientations are different (relationship between A1 and B1 or between A2 and B2), and (3) a relationship when the frequencies are different and the polarization orientations are also different (relationship between A1 and B2 or between A2 and B1) and include multiple frequencies and multiple polarization orientations as a whole, and may detect the THz waves. It is possible to arrange a plurality of unit sensors having sensitivity to components of the THz waves including three or more kinds of frequencies and three or more kinds of polarization orientations.

Figure 25:
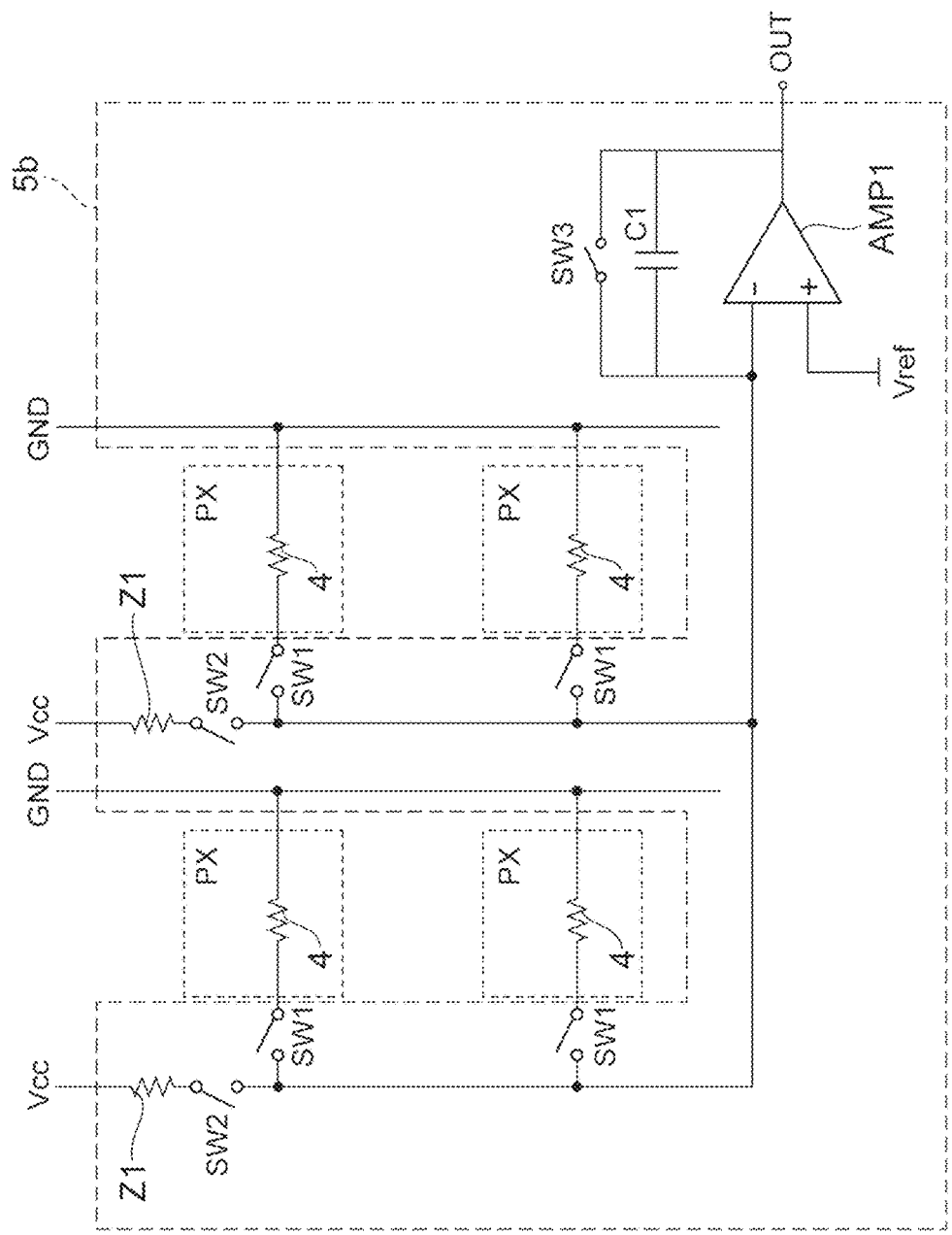
FIG. 25 is a circuit diagram of the read circuit.

FIG. 25 is a circuit diagram of the read circuit 5b in a case where the plurality of pixels PX (unit sensors) is included in the capturing area IMG. The connection in the circuit means electrical connection.

Heat generated in the resistor of the reception antenna of each pixel PX is input to the bolometer 4 having the resistor layer. Each bolometer 4 is connected to the non-inverting input terminal of the amplifier AMP1 through the switch SW1 connected to the bolometer. The bolometer 4 of each pixel PX is connected to the resistor Z1 through the switch SW1 and the switch SW2, and the resistor Z1 is connected to the power supply potential Vcc. In a case where the switch SW2 is closed in the pixels PX lined up along one column direction (ON), if the switch SW1 is closed (ON) in a desired row, an output current from the bolometer 4 of the pixel PX positioned in its address is input to the amplifier AMP1, and an output signal OUT is output from the output terminal of the amplifier AMP1.

The capacitor C1 and the switch SW3 are connected in parallel between the non-inverting input terminal and the output terminal of the amplifier AMP1, and the non-inverting input terminal is connected to the reference potential Vref. The non-inverting input terminal is connected to the connection point between the switch SW2 and the switch SW1 of each pixel PX, and the connection point is connected to the power supply potential Vcc through the switch SW2 and the resistor Z1. If the switch SW3 is closed, the circuit enters a reset state, and the capacitor C1 is discharged. If the switch SW1 positioned in a target address and the switch SW2 connected to the switch SW1 are closed after the switch SW3 is opened, a current flows to a ground potential GND from the power supply potential Vcc through the bolometer 4, and a value depending on the resistance value is input to the non-inverting input terminal of the amplifier AMP1. A charge is accumulated in the capacitor C1, and an output signal OUT is acquired from the output terminal.

After the switch SW2 positioned in a n-th column is closed, if the switches SW1 positioned in a m-th row, a (m+1)-th row, a (m+2)-th row, . . . which belong to this column are sequentially closed, signals of the pixels PX belonging to the n-th column are sequentially read (here, m and n are natural numbers). After the switch SW2 positioned in a (n+1)-column is closed, if the switches SW1 positioned in a m-th row, a (m+1)-th row, a (m+2)-th row, . . . which belong to this column are sequentially closed, signals of the pixels PX belonging to the (n+1)-th column are sequentially read. The reading is repeated in this manner, and thus, data items of the pixels PX of the entire capturing area may be output to the outside through the amplifier AMP1.

The data items of the pixels PX may be serially read through one amplifier AMP1. For example, if the amplifier is provided for each column, the data items of the pixels PX may be simultaneously read from the pixel columns in parallel.

Figure 26:
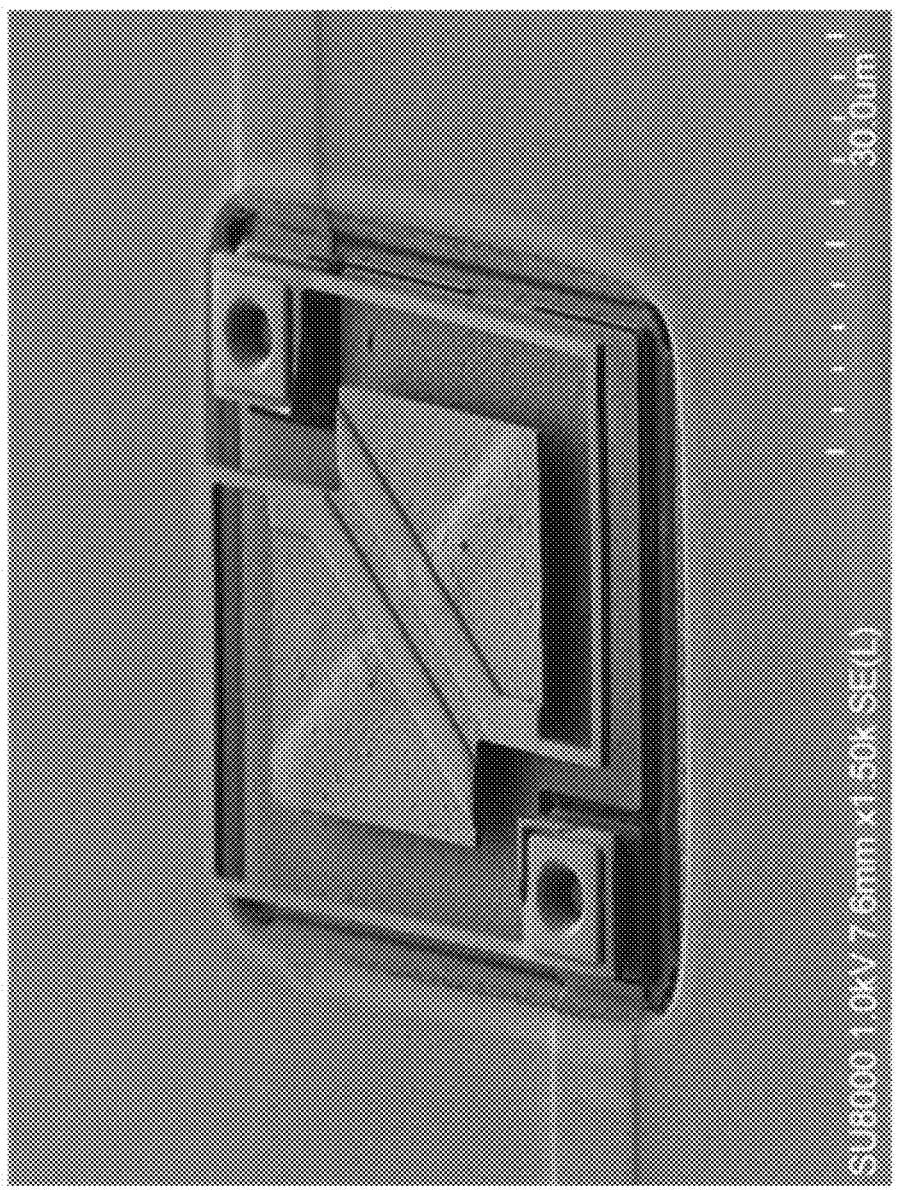
FIG. 26 is a diagram showing an electron microscope image of the unit sensor.

FIG. 26 is a diagram showing a scanning electron microscope graph (SEM image) of the unit sensor. The directional antenna is not shown in this drawing. The entire shape of the unit sensor has a square, and a length of one side is about 30 µm. The unit sensor may be formed using a photolithography technology.

Figure 27:
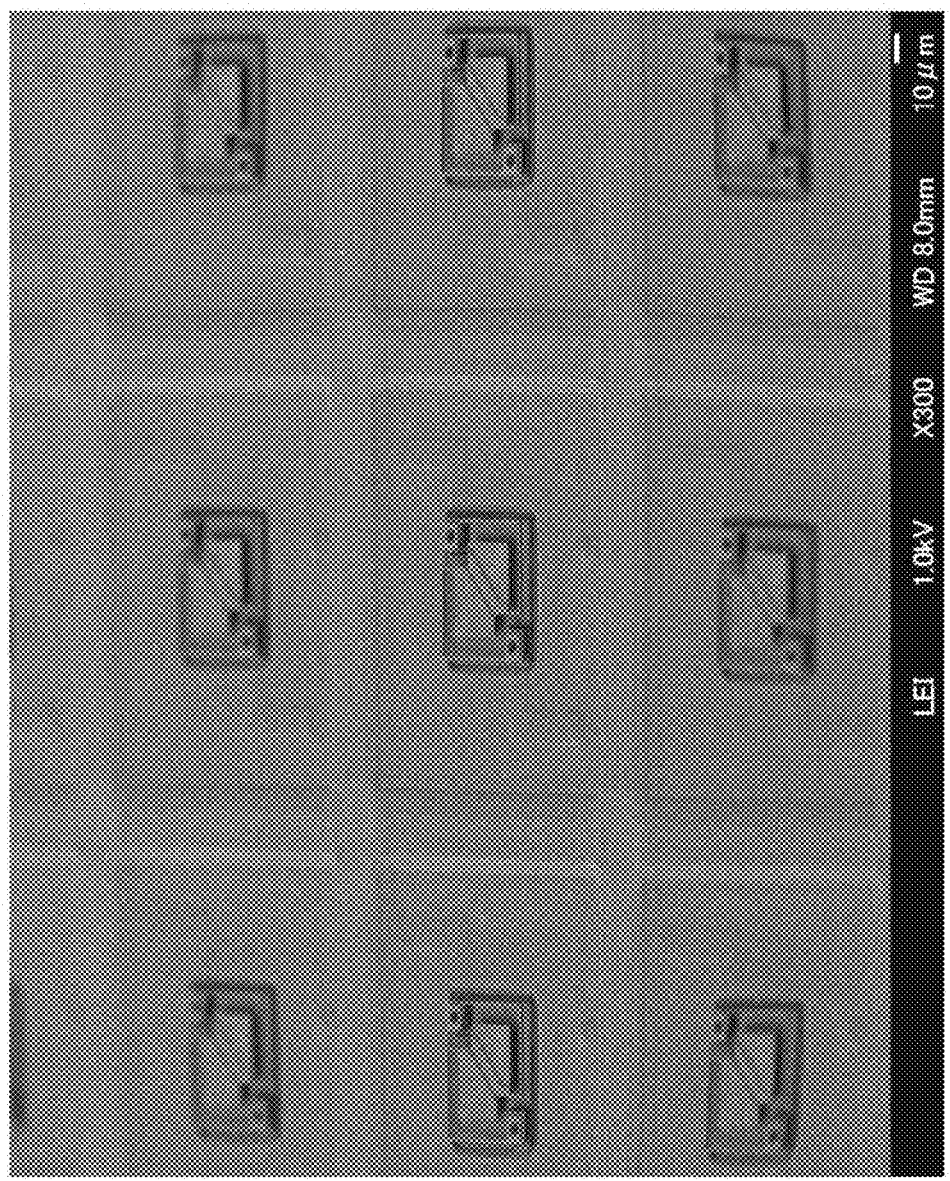
FIG. 27 is a diagram showing an electronic microscope image of a plurality of unit sensors arranged in a matrix shape.

FIG. 27 is a diagram showing a scanning electronic microscope graph (SEM image) of the unit sensors arranged in a matrix shape. One unit sensor is provided within one pixel, and a plurality of pixels is lined up in a matrix shape. These unit sensors are formed on the semiconductor substrate constituting the support substrate. In the present example, pieces of wiring for delivering signals are formed in a lattice shape in plan view, and one unit sensor constituting a pixel within an area surrounded by the pieces of wiring is formed.

FIG. 28 is a plan view of a unit pixel including the plurality of unit sensors.

Although it has been described in the above-described example that one unit sensor may be formed within one pixel, the plurality of unit sensors may be included in one pixel. These unit sensors receive THz waves having different frequencies and/or polarization orientations to be sensitive. As an example, unit sensors A1 and A2' that receive THz waves of which the polarization orientations are the same and the frequencies are different are shown in this drawing.

The unit sensor A1 and the unit sensor A2' have the same basic structures as those of the pixels PX shown in FIG. 6 or 11, and includes the directional antenna 1 (not shown in FIG. 28), the reception antenna 2, the reflection antenna 3R shown in FIG. 6 or FIG. 11. Conditions in which the respective antennas satisfy are the same as those described above, and the longitudinal directions of the directional antenna 1 and the reception antenna 2 match each other. Although a shape of the reflection antenna 3R is simplified as a square, two neighboring sides constituting the square extend so as to match each other in the X-axis direction and the Y-axis direction.

The reception antenna 2 includes a dipole antenna 2a including a pair of linear antennas, and a resistor 2b provided in a gap between the linear antennas constituting the dipole antenna 2a. The resistor 2b electrically connects the pair of linear antennas, and generates heat due to a current flowing in these antennas.

Both the longitudinal directions of the reception antennas 2 of the unit sensor A1 and the unit sensor A2' match the y-axis direction, and the dimensions thereof in the y-axis direction are different. Accordingly, in a case where the THz waves having different frequencies are received, the reception antennas of the unit sensors A1 and A2' oscillate with the received THz waves, and currents flow to the antennas. The dimensions of the reception antennas 2 in the x-axis direction may be different.

The unit pixel shown in this drawing may be provided alone within the capturing area, or the unit pixels may be arranged in a matrix shape. In both the cases, the capturing area is the enclosed space between the support substrate and the lid member.

Figure 29:
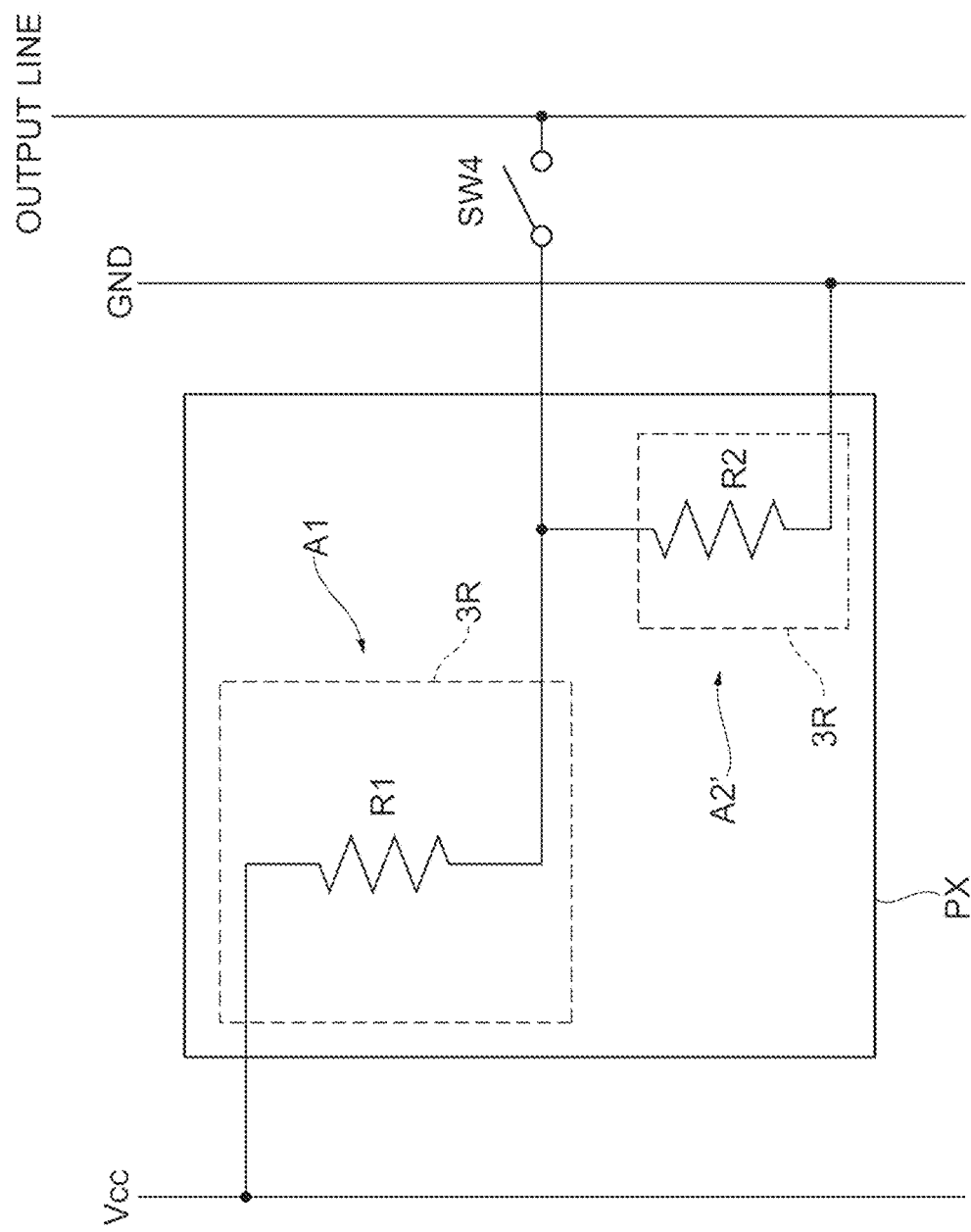
FIG. 29 shows a circuit diagram of the unit pixel.

FIG. 29 shows an example of a circuit diagram of the unit pixel shown in FIG. 28.

It is assumed that the unit sensor A1 and the unit sensor A2' are arranged within one pixel PX and the resistors of the bolometers 4 (resistor layers 4c: see FIG. 11) are R1 and R2. The resistor R1 is connected between a power supply potential Vcc and an output line OUTPUT, and the resistor R2 is connected between the resistor R1 and the ground potential GND. Accordingly, potential in a node between the resistor R1 and the resistor R2 is input to the output line OUTPUT through the switch SW4. If resistance values of the resistors R1 and R2 are expressed as the same symbols, potential in node=Vcc×R2/(R1+R2)=Vcc×1/(R1/R2+1), and the potential in this node is changed depending on a strength ratio between the THz waves detected in the unit sensors A1 and A2'.

As the potential of the output line OUTPUT, the potential in the node is greatly changed if a difference (R1−R2) is large. For example, in a case where intensity of a first frequency component is I1 and intensity of a second frequency component is I2, a voltage depending on a ratio or a difference between the intensity I1 and the intensity I2 is applied to the output line OUTPUT.

Difference images of components thereof may be acquired by arranging two reception antennas having different reception characteristics within the same pixel and detecting a difference between output voltages thereof by a differential amplifier (not shown). Alternatively, the reception antennas may be arranged by calculating the difference by inputting output voltages to a memory of the controlling device (see FIG. 12). In a case where a difference between outputs of the bolometers corresponding to the antennas having sensitivity to different frequencies is calculated, an image corresponding to a difference between images of the frequencies is acquired, and in a case where a difference between outputs of the bolometers corresponding to the antennas having sensitivity to different polarization orientations is calculated, an image corresponding to a difference between images of the polarization orientations is acquired.

Figure 30:
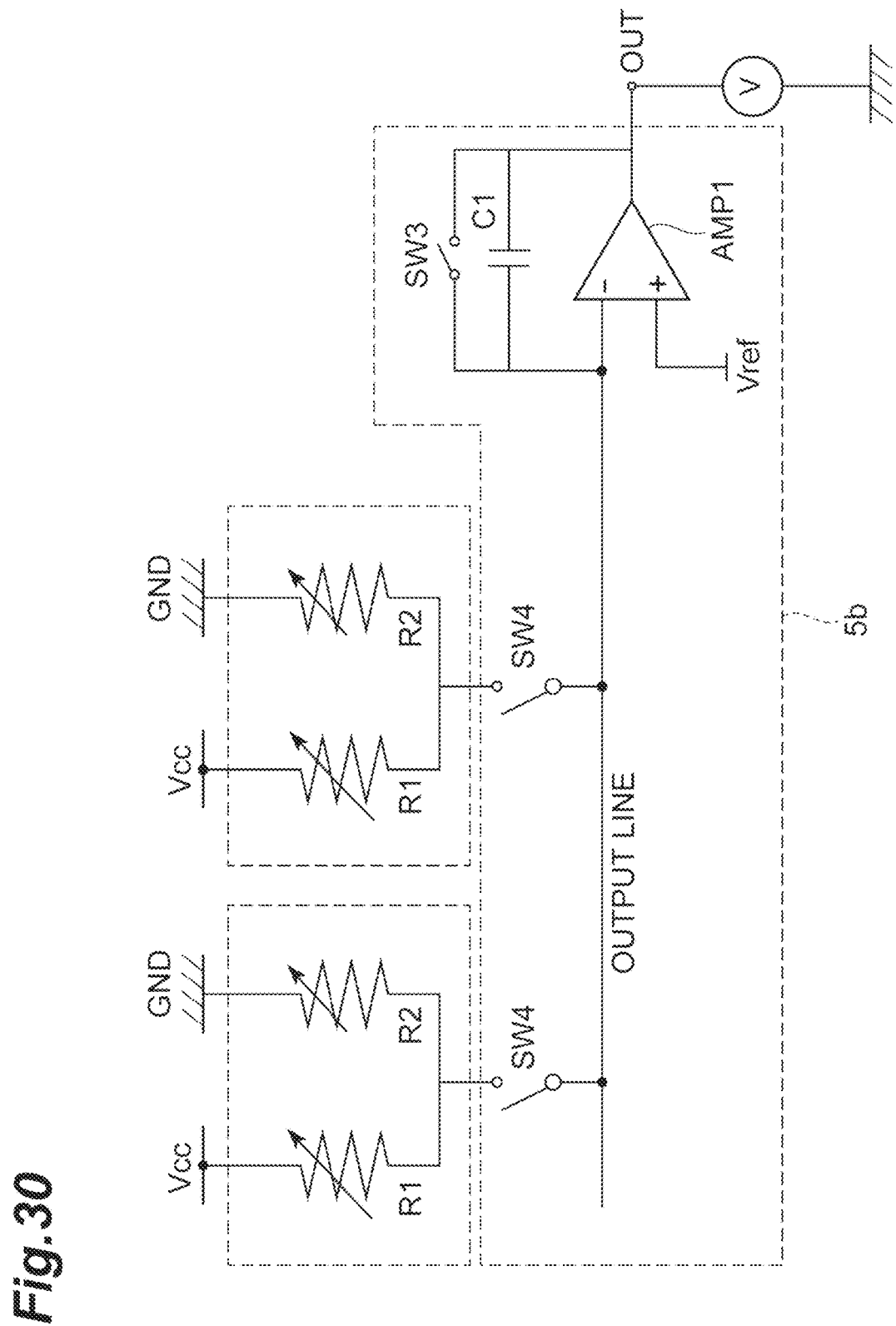
FIG. 30 shows a circuit diagram of the read circuit.

FIG. 30 shows an example of a circuit diagram of the read circuit 5b.

The read circuit may be applied to a case where two or more unit sensors are provided for one pixel as shown in FIG. 29, or may have a configuration in which two or more arbitrary unit sensors are connected in parallel and a connection point thereof is connected to the output line OUTPUT LINE. If values of two resistors R1 and R2 are changed by the THz waves incident on the reception antennas, the switch SW4 is closed (ON), and thus, voltages depending on strength ratios between the incident THz waves are sequentially input to the amplifier AMP1 from the pixels (a dotted area surrounding the resistors R1 and R2).

Outputs (divided voltage outputs of the resistor R1 and the resistor R2) of the bolometers 4 of the pixels are input to the amplifier AMP1 through the switch SW4, and the output signal OUT is output from the output terminal of the amplifier AMP1. The capacitor C1 and the switch SW3 are connected in parallel between the non-inverting input terminal and the output terminal of the amplifier AMP1, and the non-inverting input terminal is connected to the reference potential Vref.

The non-inverting input terminal is connected to the switch SW4, and the switch SW4 is connected to a connection point between the resistor R1 and the resistor R2. If the switch SW3 is closed, the circuit enters a reset state, and the capacitor C1 is discharged. After the switch SW3 is opened, if the switch SW4 is closed, a current flows to the ground potential GND from the power supply potential Vcc through the resistor R1 of the bolometer, and values corresponding to the resistance values of the resistor R1 and the resistor R2 are input to the non-inverting input terminal of the amplifier AMP1. Thus, charge is accumulated in the capacitor C1, and the output signal OUT is acquired from the output terminal. The output signal may be measured by a voltmeter V.

In a case where the resistors of the bolometers of the antennas having different reception characteristics which are arranged in different pixels are respectively R1 and R2, the reception antennas may be operated similarly to the above-described case. In a case where the outputs of the resistors R1 and R2 of the antennas having different reception characteristics which are arranged in different pixels are independently input to the differential amplifier (not shown), a difference between the outputs thereof is acquired. In a case where the outputs thereof are independently stored in the memory of the controlling device (see FIG. 12) and a difference is calculated, difference images having different reception characteristics (frequencies and/or polarization orientations) are acquired. The acquired images may be output to the display device (see FIG. 12).

REFERENCE SIGNS LIST

1 Directional antenna, 2 Reception antenna, 3 Reflection antenna, 4 Bolometer

What is claimed is:
1. A THz bolometer detector comprising:
a directional antenna that receives a THz wave, and radiates the received THz wave;
a reception antenna that is provided so as to face the directional antenna;
a bolometer that detects heat generation due to a current flowing in the reception antenna,
a lid member that includes a recess portion; and
a support substrate that is covered with the lid member, and defines an enclosed space in cooperation with the lid member,
wherein the directional antenna overlaps the reception antenna in plan view,
wherein a longitudinal length of the directional antenna is less than a longitudinal length of the reception antenna,
wherein the directional antenna is fixed to a bottom surface of the recess portion, and
wherein the directional antenna, the reception antenna, and the bolometer are provided within the enclosed space.

2. The THz bolometer detector according to claim 1, wherein a wavelength of the THz wave is $\lambda$, and
a distance between the directional antenna and the reception antenna is equal to or less than $\lambda/4$.

3. The THz bolometer detector according to claim 2, further comprising:
a reflection antenna that is provided in a position where the reception antenna is interposed between the reflection antenna and the directional antenna.

4. The THz bolometer detector according to claim 1, further comprising:
a reflection antenna that is provided in a position where the reception antenna is interposed between the reflection antenna and the directional antenna.

5. The THz bolometer detector according to claim 1,
wherein the lid member includes a silicon substrate having the recess portion,
a depth d1 of the recess portion of the silicon substrate is equal to or greater than 10 μm and is equal to or less than 400 μm,
a thickness d2 of a peripheral portion of the silicon substrate is equal to or greater than 200 μm and is equal to or less than 2 mm, and
a pressure less than an atmospheric pressure is set within the enclosed space.

6. The THz bolometer detector according to claim 5, further comprising:
an anti-reflection film that is formed on a surface opposite to the recess portion of the silicon substrate; and
an insulation film that is formed on an internal surface of the recess portion of the silicon substrate,
wherein a material of the anti-reflection film is $SiO_2$ or poly(para-xylylene),
a material of the insulation film is $SiO_2$ or poly(para-xylylene), and
a resistivity of the silicon substrate is set to be equal to or greater than 1 kΩcm.

7. A THz bolometer detector comprising:
a directional antenna that receives a THz wave, and radiates the received THz wave;
a reception antenna that is provided so as to face the directional antenna;
a bolometer that detects heat generation due to a current flowing in the reception antenna; and
a reflection antenna that is provided in a position where the reception antenna is interposed between the reflection antenna and the directional antenna,
wherein the directional antenna overlaps the reception antenna in plan view, and
a longitudinal length of the directional antenna is less than a longitudinal length of the reception antenna.

* * * * *